US012788932B2

(12) United States Patent
Yeates et al.

(10) Patent No.: US 12,788,932 B2
(45) Date of Patent: Nov. 10, 2026

(54) AEROSOL DRUG INSPIRATORY WITH RESPIRATORY SUPPORT CAPABILITY

(71) Applicant: KAER BIOTHERAPEUTICS CORPORATION, Escondido, CA (US)

(72) Inventors: Donovan B Yeates, Escondido, CA (US); Humam Al-Baidhani, Escondido, CA (US); Sai Siva Kare, Valley Center, CA (US)

(*) Notice: Subject to any disclaimer, the term of this patent is extended or adjusted under 35 U.S.C. 154(b) by 769 days.

(21) Appl. No.: 18/206,055

(22) Filed: Jun. 5, 2023

(65) Prior Publication Data

US 2024/0399099 A1 Dec. 5, 2024

(51) Int. Cl.
*A61M 16/14* (2006.01)
*A61M 11/00* (2006.01)
(Continued)

(52) U.S. Cl.
CPC .......... *A61M 16/14* (2013.01); *A61M 11/001* (2014.02); *A61M 11/02* (2013.01); (Continued)

(58) Field of Classification Search
CPC ..... B05B 7/0483; A61M 16/14; A61M 11/02; A61M 11/06; A61M 16/202;
(Continued)

(56) References Cited

U.S. PATENT DOCUMENTS 6,729,334 B1 * 5/2004 Baran ............... A61M 16/0463 128/207.14
7,802,569 B2 * 9/2010 Yeates .................. A61M 11/042 128/200.14
(Continued)

FOREIGN PATENT DOCUMENTS

AU 2016402362 B2 3/2022
CN 105499003 A * 4/2016 ............... B05B 7/12
(Continued)

OTHER PUBLICATIONS

English translation for CN 105499003, machine translated by espacenet.com.*
(Continued)

*Primary Examiner* — Tu A Vo
(74) *Attorney, Agent, or Firm* — Schlee IP International, PC; Alexander R. Schlee; Pascal A. Schlee

(57) ABSTRACT

A system and a method for generating a respirable aerosol from a liquid solution or liquid suspension. A liquid solution or liquid suspension is supplied at a liquid pressure, and a pressurized aerosolizing gas is supplied at a pressurized aerosolizing gas pressure to an aerosol generating nozzle having an aerosol exit orifice through which the liquid solution or liquid suspension is released into an aerosolizing space. Controlling the pressure of an aerosolizing gas by a controller modulates a gas pressure of the pressurized aerosolizing gas in the aerosolizing space to alternatingly exceed above and drop below a fluid pressure at the fluid exit, controlling an aerosol generation duration by the time the pressurized aerosolizing gas pressure is kept by the controller below the fluid pressure at the fluid exit.

26 Claims, 11 Drawing Sheets

(51) Int. Cl.

| | |
|---|---|
| ***A61M 11/02*** | (2006.01) |
| ***A61M 11/06*** | (2006.01) |
| ***A61M 15/00*** | (2006.01) |
| ***A61M 16/00*** | (2006.01) |
| ***A61M 16/08*** | (2006.01) |
| ***A61M 16/20*** | (2006.01) |

(52) U.S. Cl.
CPC .......... *A61M 11/06* (2013.01); *A61M 16/024* (2017.08); *A61M 16/201* (2014.02); *A61M 16/202* (2014.02); *A61M 16/208* (2013.01); *A61M 15/0086* (2013.01); *A61M 16/0808* (2013.01); *A61M 16/209* (2014.02); *A61M 2202/0208* (2013.01); *A61M 2202/025* (2013.01); *A61M 2202/0488* (2013.01); *A61M 2205/3331* (2013.01); *A61M 2205/502* (2013.01)

(58) Field of Classification Search
CPC ............ A61M 16/208; A61M 15/0086; A61M 16/0808; A61M 16/024; A61M 16/201; A61M 16/209; A61M 2202/0208; A61M 2202/025; A61M 11/001; A61M 2202/0468; A61M 2202/0488; A61M 2205/3331; A61M 2205/502
See application file for complete search history.

(56) References Cited

U.S. PATENT DOCUMENTS

| | | | | |
|---|---|---|---|---|
| 8,820,662 | B2 | 9/2014 | Yeates | |
| 9,573,147 | B1 * | 2/2017 | Yeates | A61M 11/001 |
| 9,937,303 | B1 * | 4/2018 | Yeates | A61M 11/06 |
| 10,661,033 | B2 | 5/2020 | Yeates et al. | |
| 2018/0099106 | A1 * | 4/2018 | Yeates | B05B 7/0815 |
| 2019/0160232 | A1 * | 5/2019 | Yeates | B05B 7/045 |
| 2020/0276400 | A1 * | 9/2020 | Yeates | A61M 15/0086 |

FOREIGN PATENT DOCUMENTS

| | | | | | |
|---|---|---|---|---|---|
| CN | 109562237 | B | | 8/2021 | |
| CN | 218944144 | U | * | 5/2023 | B05B 7/04 |
| JP | 6743280 | B2 | | 8/2020 | |
| WO | WO-2020241098 | A1 | * | 12/2020 | B05B 5/0533 |

OTHER PUBLICATIONS

English translation for CN 218944144, machine translated by espacenet.com.*

* cited by examiner

Section A-A

Section B-B

Section C-C

Section D-D

Section E-E

Section F-F

AEROSOL DRUG INSPIRATORY WITH RESPIRATORY SUPPORT CAPABILITY

GOVERNMENT SUPPORT

The present invention, in part, was supported by the National Institute of Health, Heart, Lung and Blood Institute under grants R44HL142335 and R43HL127834. The US government has certain rights to this invention.

BACKGROUND OF THE INVENTION

Therapeutic aerosol inhalations are deposited in the respiratory tract to treat respiratory diseases and syndromes. More widespread usage of aerosol delivery devices has led to marked improvement in respiratory function and mortality, especially those devices capable of safely delivering small molecules and micrograms of the therapeutics. However, there is an unmet need to more effectively treat those patients with more severe respiratory distress due to multiple etiologies. While respiratory distress impacts people of all ages, the young and elderly are among those most vulnerable to such ailments. In addition to high cost of health care, these demographics of patients are associated with high mortality rates.

Globally, over 120 million episodes of pneumonia in children under the age of 5 are reported annually, 14 million of which progress to severe episodes, and 888,000 result in death. Most of these patients are less than 2 years of age. Other illnesses such as Idiopathic Pulmonary Fibrosis (IPF), TB, COVID-19 and Chronic Obstructive Pulmonary Disease (COPD) also require effective deposition of the minimum concentrations of antivirus vaccines or anti-infectives throughout the lungs for positive outcomes. Moreover, lifesaving rescue therapy for hypoxemia patients requires noninvasive treatments with pulmonary surfactant aerosols having life-saving biophysical properties.

Many potential therapeutic treatments with aerosols fail due to inadequate deposition of the active agent into the distal lungs to resolve physiological dysfunction or disease malady. The death rate of 40% of patients suffering from respiratory distress, which includes neonates, infants, children and adults, is unacceptable. Delivery of insufficient masses of agents to the lungs using present inadequate aerosol devices cannot be expected to achieve a therapeutic benefit, and therefore should not be used.

Atomizers generate aqueous aerosols of ~3 μm diameter at output flows of 0.3 ml/minute using Venturi liquid flow. Compressed central axial air flow creates a negative Venturi liquid flow to the aerosolizing nozzle where the plume is generated by Raleigh breakup phenomena. Larger droplets are recirculated. Output aerosol flow in these systems is typically 0.3 ml/minute with 12 L/minute gas flow.

Mesh nebulizers include a vibration mesh typically having one thousand holes, each 3 micron in size, and vibrate at 128,000 cycles per second. Aerosol generation in these mesh nebulizers is severely limited by the drug liquid viscosity. Generally, viscosities greater than 6 cP markedly reduce aerosol generation or even prevent it altogether. Moreover, the mesh is susceptible to cloggage by liquid suspensions and large molecular entities. The output rates in these systems are limited to less than 1 ml/min. These devices have been incorporated with separate ventilators to provide aerosol therapy in conjunction with respiratory support.

Windtree's capillary aerosol generation system incorporates Sinclair-Lamer aerosol generation. Evaporation of liquids results in aerosol nuclei. Condensation of the vapor on the nuclei results in uniform aerosols. This method can generate surfactant aerosols at 3 l/min through a delivery tube through the nose of a neonate. Losses in the aerosol generation system and tubing, combined with minute volumes of 20-40 ml/breath, results in delivery of only approximately 1% of the initial volume of the surfactant liquid loaded to the drug vial for delivery.

Trudell's Solarys nebulizer uses compressed air pressure. Using this device, aerosolization occurs external to the liquid feed tip and its surrounding compressed gas ports. Generally, larger aerosol diameters and broader sprays are generated with large particle size dispersion. However, high exit gas port pressures and aerosol velocities can cause injury and local impaction in the oral cavity or conducting airways in the lungs.

There is an unmet need to generate aerosols with a range of effective therapeutic moiety agents, from both low to high concentrations of drugs, over a range of low and high molecular weights, structural configurations, as well as low and high viscosities. Aerosol drugs delivered using nebulizers include broncho dilators, antibiotics, mucolytics and future biologics that include pulmonary surfactant, proteins, oligomers antibodies nano suspensions.

Generation of fine atomized aqueous aerosols suitable for penetration through the upper respiratory airways and deposition in the peripheral lungs of neonates, infants and children with low tidal and minute volumes is a challenge due to the high gas volumes and high jet velocities required, as predicted by the Weber number. Thus, pediatric patients typically inhale only a small volume of aerosol. These limitations have resulted in a preference to use mesh nebulizers as a medication delivery system, despite the aforementioned disadvantages and limitations.

It is therefore an object of the invention to provide an aerosol delivery system and method that overcomes the aforementioned shortcomings in the prior art. This object is achieved as by the various embodiments of this disclosure ("AeroPulsR"), which overcomes these challenges by use of its inventive liquid aerosol dispensing system to provide suitable inhalation therapeutics for treatment of a wider range of illnesses and patients.

Efficiently generating and delivering fine aqueous aerosols using pressure driven nozzles, for instance as described in the U.S. Pat. No. 10,661,033, herewith incorporated by reference, during inspiration in children requires that small volumes of the plumes from the nozzle are either delivered directly and/or reduced in velocity using a mini aerosol concentrator as described in this specification.

To achieve this capability, aerosol generation must be able to be started and stopped within milliseconds. The fine particle generation by the aforementioned nozzle utilizes pressurized drug containing liquids along with pressurized gas such as air, oxygen or heliox. Previously, a high-pressure syringe drive was used to deliver the liquid to the nozzle. This syringe was considered to be too specialized and cumbersome to be used by untrained operators, and leakage and misuse routinely resulted in liquid spillage. Additionally, the syringe drive was unable to respond to the rapid changes of liquid flow to the nozzle necessary to meet the rapid temporal precise dosimetry requirements during inspiratory breaths in pediatric patients. The required rapid precise control of aerosol delivery during the inspiratory phase, especially for neonates and infants.

SUMMARY OF THE INVENTION

In one general aspect of the invention, an aerosol generating nozzle system is provided for generating a respirable aerosol from a liquid solution or liquid suspension. The system may include an aerosol generating nozzle having an aerosol exit orifice. The aerosol generating nozzle system may also include a fluid source for supplying the liquid solution or liquid suspension to be aerosolized through a liquid supply line to an input of the aerosol generating nozzle at a liquid pressure. The aerosol generating nozzle system may furthermore include a first gas supply line connected to gas input of the nozzle for supplying pressurized aerosolizing gas at a pressurized aerosolizing gas pressure to the nozzle. The aerosol generating nozzle system may in addition include a first controllable valve for modulating the pressurized aerosolizing gas pressure. The aerosol generating nozzle system may moreover include a controller connected to the first controllable valve for controlling the same to modulate the pressurized aerosolizing gas pressure. The controller of the aerosol generating nozzle system may furthermore be configured to modulate the pressurized aerosolizing gas pressure so that alternatingly a gas pressure of the pressurized aerosolizing gas in the aerosolizing space exceeds and drops below a fluid pressure at the fluid exit in an alternating fashion, where an aerosol generation pulse duration is controlled by the time the pressurized aerosolizing gas pressure is kept by the controller below a fluid pressure at the fluid exit. The aerosol generation duration can be controlled within wide ranges, ranging from pulses as short as 10 ms to a quasi-continuous aerosol generation of several minutes. During the inhalation cycle, a plurality of pulses can be delivered to the patient, while aerosol generation may be shut off completely during the exhalation cycled. It is also possible to make the aerosol generation continuous over the entire inhalation cycle, and stop the aerosol generation completely during the exhalation phase, so that the pulse length of aerosol generation spans over the entire inhalation phase. The nozzle of the aerosol generating nozzle system may include an internal aerosolizing space connected to at a fluid exit where the liquid solution or liquid suspension enters the aerosolizing space and a pressurized aerosolizing gas exit where the pressurized aerosolizing gas enters the aerosolizing space encompassing the fluid exit.

DETAILED DESCRIPTION OF THE INVENTION

The first controllable valve of the aerosol generating nozzle system may have an input end, an output end and a first adjustable pressure regulator provided upstream of the input end of first controllable valve for regulating the pressure at the input end of first controllable valve and therefore limiting a maximum pressure at the output end of the first controllable valve when it assumes its fully open configuration.

The aerosol generating nozzle system may further include a second controllable valve for adjusting the liquid pressure in the liquid supply line. Additionally, the fluid source may be a container having an input connected to a second gas supply line and an output connected to the liquid supply line, and the second controllable valve may be provided in the second gas supply line for modulating a second gas pressure that equals the liquid pressure in the container, where the controller controls the second controllable valve.

The controller of the aerosol generating nozzle system may be configured to hold the second gas pressure that equals the liquid pressure in the container essentially constant while performing several duty cycles of modulating the pressurized aerosolizing gas pressure so that the gas pressure of the pressurized aerosolizing gas in the aerosolizing space exceeds and drops below in an alternating fashion while maintaining the essentially constant fluid pressure at the fluid exit.

The liquid supply line of the aerosol generating nozzle system may be constructed of a compressible material and include a solenoid pinch valve in the liquid supply line for additionally turning the liquid volume flow on or off.

The controller may be configured to control the first valve and second valve so that aerosol generation takes place while the aerosol delivery channel port is controlled to be open for inhalation by the bidirectional valve assembly, and conversely the aerosol generation is stopped by controlling the first valve and the second valve while the bidirectional valve assembly has closed the aerosol delivery channel port while opening an aspiration port for enabling exhaling by a patient.

The aerosol generating nozzle system may further comprise a check valve provided in the liquid supply line, configured to prevent a volume flow back from the nozzle towards the fluid source.

The aerosol generating nozzle system may include the second controllable valve configured to include an input end and an output end, and a second adjustable pressure regulator may be provided upstream of the input end of the second controllable valve for regulating the pressure at the input end of the second controllable valve and therefore limiting a maximum pressure at the output end of the second controllable valve when it assumes its fully open configuration.

The aerosol generating nozzle system may further include: an aerosol chamber connected with the aerosol exit orifice to receive aerosol exiting through the aerosol exit orifice into the aerosol chamber; and a counterflow gas tube having a counterflow gas tube exit opening opposite of the aerosol exit orifice and spaced therefrom for arresting the aerosol exiting through the aerosol exit orifice into the aerosol chamber.

The aerosol generating nozzle system may include the counterflow gas tube connected via a counterflow gas tube supply line with a gas source, and a third controllable valve provided in the counterflow gas tube supply line for modulating a third gas pressure in the counterflow gas tube, wherein the controller controls the third controllable valve.

The aerosol generating nozzle system may include the third controllable valve configured to include an input end and an output end and a third adjustable pressure regulator may be provided upstream of the input end of the third controllable valve for regulating the pressure at the input end of third controllable valve and therefore limiting a maximum pressure at the output end of the third controllable valve when it assumes its fully open configuration.

The aerosol generating nozzle system may be configured to have the aerosol chamber comprise an aerosol chamber input end accommodating the aerosol exit orifice, and the counterflow tube and an aerosol chamber output end downstream of the aerosol exit orifice and the counterflow tube, wherein said aerosol chamber output end is connected to a concentrator dividing an aerosol volume flow through the aerosol chamber in a respirable volume flow including a least 70% of aerosol particles at a concentrator respirable aerosol output end and an exhaust volume flow including 30% or less of the aerosol particles at a concentrator exhaust gas output end.

The aerosol generating nozzle system may include a bidirectional valve assembly having a bidirectional valve assembly input that connects with the concentrator respirable aerosol output end, alternatingly opening the aerosol delivery channel port while closing an aspiration port for enabling inhaling of the aerosol by a patient, and conversely closing the aerosol delivery channel port while opening an aspiration port for enabling exhaling by a patient.

The aerosol generating nozzle system may include a pressure relief valve connected to a plenum through which the respirable aerosol volume flow passes prior to inhaling by a patient for keeping the pressure of the respirable aerosol to be inhaled by a patient at a predefined pressure.

The aerosol chamber of the aerosol generating nozzle system may include an aerosol chamber input end accommodating the aerosol exit orifice and the counterflow tube, and an aerosol chamber output end downstream of the aerosol exit orifice and the counterflow tube, wherein said aerosol chamber output end is connected to an output cone.

The aerosol generating nozzle system may include a bidirectional valve assembly having a bidirectional valve assembly input that connects with the output cone, alternatingly opening the aerosol delivery channel port while closing an aspiration port for enabling inhaling of the aerosol by a patient, and conversely closing the aerosol delivery channel port while opening an aspiration port for enabling exhaling by a patient. In another general aspect of the invention, a method is provided for generating a respirable aerosol from a liquid solution or liquid suspension using an aerosol generating nozzle system. The method may include supplying liquid solution or liquid suspension at a liquid pressure, and supplying a pressurized aerosolizing gas at a pressurized aerosolizing gas pressure to an aerosol generating nozzle having an aerosol exit orifice. The method of generating a respirable aerosol using an aerosol generating nozzle system a respirable aerosol may also include releasing the liquid solution or liquid suspension and pressurized aerosolizing gas into an aerosolizing space encompassing a fluid exit ejecting the liquid solution or liquid suspension into the aerosolizing space where an aerosol is generated. The method may furthermore include controlling a liquid pressure and an aerosolizing gas pressure by a controller. The method may in addition include modulating at least the pressurized aerosolizing gas pressure so that alternatingly a gas pressure of the pressurized aerosolizing gas in the aerosolizing space exceeds and drops below a fluid pressure at the fluid exit, controlling an aerosol generation pulse duration by the time the pressurized aerosolizing gas pressure is kept by the controller below the fluid pressure at the fluid exit. The method may include shutting off the supply of liquid solution or liquid suspension by shutting off a liquid supply line.

The method may include modulating a third gas pressure in a counterflow gas tube opposing the aerosol exit orifice for arresting the aerosol exiting the aerosol exit orifice into an aerosol chamber connected with the aerosol exit orifice.

The method may include a pressure relief valve connected to a plenum through which a respirable aerosol volume flow passes for keeping the pressure of the respirable aerosol to be inhaled by a patient at a predefined pressure.

The method may include alternatingly opening an aerosol delivery channel port while closing an aspiration port for enabling inhaling of the respirable aerosol by a patient, and conversely closing the aerosol delivery channel port while opening the aspiration port for enabling exhaling by a patient. The first valve and second valve may be controlled such that aerosol is only generated while the aerosol delivery channel port is controlled to be open for inhalation, and conversely aerosol generation is stopped by controlling the first valve and the second valve while the aerosol delivery channel port while opening an aspiration port for enabling exhaling by a patient.

The method may include concentrating the aerosol by a concentrator dividing the aerosol volume flow into a respirable volume flow including a least 70% of aerosol particles at a concentrator respirable aerosol output end and an exhaust volume flow including 30% or less of the aerosol particles at a concentrator exhaust gas output end.

The method may be applied to a liquid solution or liquid suspension containing a surfactant.

Using this method, a respirable aerosol having a fine particles size distribution of 1.5-6 μm MMAD may be generated.

The method may be applied to a liquid solution or liquid suspension having a viscosity of 6 to 50 cSt.

The present disclosure involves an aerosol generation system together with adjoining components to be used by a clinician for providing aerosol inhalation therapy with concurrent respiratory support. A housing may encompass several system parts including electronic components, regulators, valves, a liquid dispenser system, and an aerosol nozzle chamber. The system is controlled by a console, which includes a user interface, a microcontroller, a hardware controller, and internal hardware. The microcontroller housed in the console is responsible for communicating with the user and initiating preset commands that control the hardware controller. The hardware controller comprises a set of solenoid valves that precisely control the flow of regulated pressurized gas such as air, oxygen and/or heliox. The pressurized gas is regulated by four pressure regulators. Three regulators supply gas that control a variety of system functions, including: (i) the flow of hydraulic driven liquid from a container to a nozzle via a capillary, (ii) the liquid flow within an aerosol space, and (iii) the gas pressure and velocity for shearing the liquid to form an aerosol. The liquid drug dispenser is pressurized and is configured to deliver liquid to the nozzle. A counterflow regulator may be configured to regulate gas counterflow that decelerates the aerosol plume from the nozzle. The aerosol chamber may be configured to process the aerosol, and may further include a detachable cone which converges the generated aerosol downstream towards an aerosol delivery outlet. The delivery outlet may be configured to include a desired level of respiratory support pressure. The processed aerosol comprises fine aqueous particles effective for respiratory treatment.

A control module, also known as electronics control and interface module (ECIM), comprises components configured to control the system. The microcontroller activates a series of fast switching solenoid valves, which in turn control the onset and offset sequence of the gas flows that operate the AeroPulsR system. The internal hardware may comprise four precision regulators (Bellofarm 960-007-009 modified with bleed 803-000-001 to reduce the heliox use). A primary regulator R regulates the input pressure P for the system. The primary regulator R regulates pressurized gas from a high-pressure source and maintains the gas pressure P at a constant level, typically between 40 and 70 psi. Three additional regulators—R1, R2 and R3—regulate gas pressure P1, P2 and P3, respectively. R1/P1 correspond to the liquid drug dispenser, R2/P2 correspond to the aerosolizing nozzle, and R3/P3 correspond to the counterflow tube. Activation of these pressures is controlled by rapid action solenoid valves. The output pressures of each of the precision regulators are preset prior to delivering the aerosol drug/agent treatment to the patient. The gas flow is metered by the regulators and modulated by the solenoid valves to control a plurality of system components and parameters, including: the pressure of the liquid in the vial, the rate of flow of the liquid to the nozzle, the cessation of aerosol generation, the aerosol arresting counter-flow gas flow, and the bidirectional valve that regulates the inspiration of aerosol and expiration of the breath. The control module may have tactile, visual, and/or audible input and output elements for controlling the system and administering the therapy. A green button may be included on the electronics control and interface module (ECIM) for activating the microcontroller that controls the timing and actuation of solenoid valves. These solenoid valves enable precise aerosol generation and delivery as well as the timing of the respiration ventilation. Opening and closing of specific solenoid valve may be achieved by an Arduino microcontroller. Additionally, the control module may include a silver button for switching the device ON or OFF. The ECIM may include a simplistic layout having three LEDs and a built-in speaker, which work together to instruct the user on inhalation and exhalation timing. The prescribed treatment duration for a given patient may be pre-loaded to the ECIM in the form of software code. A therapy-specific software program may be uploaded before the treatment begins, or alternatively a pre-set therapy program may be accessed.

The pneumatic and hydraulic controls of the aerosol generation and delivery system involve a network of regulators and valves. The gas pressure of regulator R (which may be set at 60 psi), sets a maximum pressure for the entire system, followed downstream by a junction of a plurality of parallel conduits feeding the pressure from the pressure regulator R into several pressure regulators R1, R2 and R3, each of which feeding into respective downstream pressure control valves V1, V2 and V3 for fine-tuning the pressure control to fall within narrow margins of tolerance. While the 2-way control valve V1 downstream of the pressure regulator R1 controls the pressure of the liquid to be aerosolized, a 2-way control valve V2 downstream of the pressure regulator R2 controls the pressure of the gas aerosolizing the liquid and consequently the pressure in an aerosolizing space surrounding a liquid exit orifice where the liquid enters the aerosolizing space. Raising the gas pressure in the aerosolizing space by the pressure control valve V2 above the liquid pressure controlled by the pressure control valve V1 results in shutting off the liquid flow through the liquid exit orifice into the aerosolizing space, which prevents liquid aerosolization. Conversely, lowering the liquid pressure at the liquid exit orifice below the gas pressure in the surrounding aerosolizing space likewise shuts off liquid flow into the aerosolizing space. Dropping the liquid pressure can be accomplished by the pressure control valve V1 and/or the pressure regulator R1. For example, setting the pressure at the pressure regulator R1 to zero shuts down the liquid flow. However, during operation, a fine-tuning of the liquid pressure is necessary, which is accomplished by the pressure control valve V1.

During operation, it is more favorable to keep the liquid pressure at a constant value within narrow tolerances, and to modulate the gas pressure in the aerosolizing space via the pressure control valve V2. Such control can accomplish a pulsed aerosol generation, e.g. in pulses a short as 10 ms. Keeping the gas pressure in the aerosolizing space constant but modulating the liquid pressure is also possible, but tends to be a slower. Also, both the liquid pressure and the aerosolizing gas pressure may be modulated simultaneously. From a practical standpoint, keeping the liquid pressure constant within narrow margins and modulating the aerosolizing gas pressure is the preferred solution, both as to the complexity of the control, as well as the response time to a modulating signal controlling the pressure control valve V2.

For controlling the liquid pressure, the 2-way valve V1 is activated so that a gas pressure in a vial holding the liquid to be aerosolized is set, the gas pressure forcing the liquid out of the vial and into the aerosolizing nozzle where it flows through a capillary inside the nozzle that terminates at the aforementioned liquid exit orifice.

Finally, a third pressure can be controlled by the control valve V3 for a gas flow into a counterflow tube ejecting a counterflow gas, e.g. air, for "arresting" an aerosol plume that enters from the aerosolizing nozzle into an aerosol chamber. Controlling this pressure simultaneously controls the volume flow of gas exiting the counterflow tube, which in turn controls the gas flow speed of the gas exiting the counterflow tube. This does not only control the "arresting" action distributing the aerosol plume in the aerosol chamber, but also determines an amount of dilution gas diluting the aerosol in the aerosol chamber, which may be beneficial for avoiding liquid aerosol particle deposition within the aerosol chamber.

Further, a 5-2-way valve V4 is provided proximal to a patient for controlling the aerosol flow. During inspiration, the 5-2-way valve V4 opens an aerosol delivery channel to allow aerosol to flow to the patient. In contrast, during exhalation the 5-2-way valve V4 shuts off or at least reduces the aerosol flow to the patient, while simultaneously opening an aspiration port venting to outside of the system. It is also possible to synchronize the actuation of control valve V4 which is controlled in synchrony with the inhaling/exhaling cycles of the patient with the pressure modulation by the valve V2 controlling the aerosol generation, and optionally along with that to also synchronized the gas flow through the counterflow tube controlled by the pressure control valve V3.

The system may include a liquid dispenser system that enables the drug to be aerosolized to be easily loaded onto the AeroPulsR console. Moreover, the pneumatic liquid dispenser is designed to enable precise control of the aerosol delivery during the inspiratory cycle, especially for treatment of neonates and infants. The dispenser facilitates the delivery of surfactant or other viscous or non-viscous agents using the AeroPulsR system, and allows liquids of known viscosity to be precisely metered to the aerosolizing nozzle.

Compressed gas (air, heliox or oxygen) is used to pressurize the dispenser system for transporting the liquid drug into the nozzle for aerosolization. A dedicated solenoid valve precisely synchronizes the hydraulic liquid flow for aerosolization with each inspiratory breath. No mechanical liquid pumps or electronic flow devices are required. In addition, handling of the liquid dispenser is configured to be easy for clinicians and patients to use.

The liquid dispenser system may comprise a sliding mount, a cap and drug-containing vial. The sliding mount may be fixed to the AeroPulsR housing. The cap may be attached to the top of the vial, which may contain a liquid drug agent. The vial (which may for instance have a volume of 15 ml or 50 ml) may be secured to the cap with a one-handed 180° twist, simultaneously achieving easy vial loading and a leak proof seal. A capillary tube for transporting the liquid drug may extend to the bottom of the vial. The drug agent may be added to the vial as needed without changing the capillary or the nozzle. After the vial is attached to the cap, it may easily be inserted into the sliding mount affixed to the housing. This insertion may be performed with one hand, in a manner similar to filling an atomizer. The sliding mount may include two ports, namely an inlet for pressurized gas and an outlet with a capillary attachment for transporting the liquid agent to the nozzle. The cap may include corresponding gas inlet and liquid outlet ports, which mate with the mount holes via face seals. A first face seal may be included on the vial cap to seal the liquid capillary with the capillary on the cap-mount. A second face seal may be included to seal the gas pressure port. The system may also include a fluidic check valve disposed between the capillary and nozzle barrel, and may be configured to deliver the liquid in the vial to the nozzle and prevent back-flow of liquid into the vial. In a preferred embodiment, the total volume of the liquid inside the capillary and the nozzle barrel is less than 0.5 ml. The capillary feeds the liquid through the capillary to the barrel knob and through the axial channel to the liquid jet orifice through which the liquid enters the aerosolizing space. The flow rate of the viscous liquid in the vial to the nozzle is dependent on four parameters: 1) Pressure difference between the vial and nozzle chamber, 2) capillary diameter, 3) capillary length, and 4) liquid viscosity. Thus, the equation for the liquid flow rate (Q) in a capillary based on the parameters of the pressure difference (AP) across of the capillary, liquid viscosity (u), inside diameter (D), and length (L), and is given by:

$$Q = \frac{\pi\left(\frac{D}{2}\right)^4 \Delta P}{8\mu L}$$

A capillary with larger diameter may be selected for liquid agents with higher viscosities, which enables adequate liquid flow generation with a pressure differential of only 0.01 psi. This technique results in lower pressure losses in the system.

Precision regulator R provides the highest pressure to be used by the other regulators R1, R2, and R3. Precision regulator R is set at a constant pressure, for instance between 40 psi and 60 psi. This compressed gas output is connected to the inputs of R1, R2, and R3. A venting 2-way solenoid valve V1 is placed in line between R1 and the vial, and passes the gas input through a cap on the vial to pressurize the liquid in the vial. When this 2-way venting valve V1 is ON, no gas pressure is provided to the vial. When valve V1 is OFF, the regulated output pressure gas from R1 pressurizes the liquid vial and maintains a precise pressure, typically at 50 psi. A capillary tube is included with an inlet located at the bottom of the vial. The liquid from the vial passes through the capillary through an inline check valve to the nozzle.

It is noted that the liquid flow is independent of the vessel volume or its liquid contents, indicating a broader use for this liquid delivery system. The liquid dispenser system precisely meters the delivery of liquid solutions and suspensions of low or high molecular moieties with viscosities including, but not limited to, 1 to 60 cP. Notably, this novel pneumatic system is readily manufacturable, cost effective and the vial is disposable.

The system includes a unique proprietary drip-less, clog-free nozzle that allows low and high viscosity liquids to be converted into fine aqueous aerosols. This nozzle resolving current shortcomings of other nozzles by enabling generation of aqueous viscous liquids having viscosity between 1 and 60 cP. Moreover, with the present system, liquid aerosols are generated 10 times faster (0.4 ml/min up to 4 ml/min) than with current atomizers and mesh nebulizers. The system is tuned to deliver respiratory aerosols with narrow size distributions between 1-6 μm in diameter. The liquid in the vial is maintained at a constant pressure and enters through a liquid microchannel extending axially through the center of the nozzle barrel. The axial liquid microchannel is surrounded by gas microchannels. In a preferred embodiment, four radially positioned air microchannels are included within the nozzle to allow for high pressure gas to be transported into the nozzle. Either air, oxygen or heliox enters the four ports on the nozzle barrel. The input ports for the gas microchannels may be made at an acute angle of 35 degrees to assist in smooth gas inflow and reduce flow resistance. The output of the liquid nozzle and the outputs of the gas microchannels terminate at a small aerosolization space within the nozzle. Typically, the gas pressure is maintained between 30 psi and 70 psi inside the aerosolization space. Aerosolization occurs within the aerosolization space when the gas and liquid converge. The aerosol exits the nozzle through an exit orifice, and is expelled as a columnar plume within a sheath of gas essentially devoid of aerosol. The resulting generated aerosol plume forms a central columnar aerosol plume that is surrounded by a sheath of gas that prevents interaction of the aerosol with the output orifice. This results in a clean, drip and clog free nozzle resistant to exit orifice wear.

The cross section of the nozzle barrel and nozzle aerosolization space is shown United States Patent Publications U.S. Pat. No. 8,820,662 B2; U.S. Pat. No. 9,573,147 B2; and U.S. Pat. No. 10,661,033 B2, and Japanese Patent Publication JP 6743280 B2, Chinese Patent Publication CN 109562237 B, and Australian Patent Publication AU 2016402362 B2, herewith incorporated by reference. It is advantageous to have a greater number of gas channels, large gas channel diameters, and short channel lengths, as these parameters increase the gas flow rate and reduces the gas flow resistance. Collectively these conditions reduce the loss of gas pressure in the nozzle barrel and thus the aerosolization space experiences higher pressure compared to the previous nozzle, markedly improving the performance of the revised nozzle, thereby enabling the aerosol to be rapidly switched on or off.

The nozzle end contains a minute aerosolizing space where the liquid is aerosolized and transported through an exit orifice of the aerosol chamber. The present disclosure describes a novel approach for controlling the liquid flow to be aerosolized within the aerosolization space. The differential pressure between the gas in the aerosolizing space and the liquid vial (AP) controls the liquid flow rate, and thus the aerosolization rate. The pressure in the aerosolizing space is controlled by a dedicated fast switching solenoid valve. When the gas pressure is less than the liquid pressure in the aerosolization space, the liquid is aerosolized. Conversely, when the gas pressure is higher than the liquid pressure in the aerosolizing space, the liquid flow is stopped and no aerosol is generated. More specifically, liquid flows from the liquid vial to the nozzle when the pressure in the aerosolization space is less than the liquid pressure in the vial. When aerosol generation should be stopped, e.g. during a time period between aerosol generation pulses, valve V2 interchanges P2 to pressurized gas P, thereby increasing the pressure inside the aerosolization space.

Liquid flow can be stopped by increasing the pressure of the gas surrounding the liquid jet within the aerosolizing space down-stream from the aerosol exit orifice. As described by Venturi, an increase in gas pressure increases its velocity which decreases the pressure of the liquid jet.

The compressed gas within this nozzle chamber causes an extremely rapid acceleration of the liquid jet as the diameter doubles from 0.01 inch to 0.02 inch at the aerosol exit of nozzle, thereby allowing shearing and expansion of the liquid such that aerosol is generated within this space. However, the flow resistance offered by the narrow orifice in the nozzle cap increases the gas pressure within the aerosolization space. The overall result is such that despite the decrease in Venturi pressure, the summation of the pressures on the gas acting on the liquid jet arrests the liquid flow within the liquid jet nozzle.

A one-way check valve may be attached to the capillary in the dispenser cap to prevent back-flow of liquid in the nozzle and to allow liquid flow towards the nozzle cap orifice. The pressure differential between the gas and liquid is precisely controlled within 0.01 psi, and preferably within less than 0.001 psi. When aerosol generation is desired, valve V2 facilitates an interchange of pressure between P2 and P, as discussed. When the gas pressure in the aerosolization space is reduced below the liquid pressure, liquid flows into the aerosolization space and fine aerosols are generated. Precise control of gas flows and liquid flows liquid flow rate through the nozzle to be controlled between 0.5 ml/min and 4.5 ml/min. This is achieved by reducing the pressure within the aerosol space according to the viscosity of the liquid, with differential pressures constraints between 0 and 5 psi. High viscosity liquids require a higher pressure differential and/or a larger internal diameter capillary.

The gas pressure interacts with the liquid from the liquid nozzle to aerosolize the liquid into a fine plume. When the gas pressure regulated by regulator R2 is lower than the liquid pressure, the flow is proportional to the pressure differential between the liquid and the gas. When the gas pressure regulated by system regulator R is larger than 0.5 psi, the liquid flow is arrested and the aerosol generation stops. This sequence is repeatable as needed. The pressure in the vial is vented to the atmosphere via the vent valve V1, and closing vent valve V1 prevents the pressure in the vial from increasing. This stops further liquid entering the nozzle and prevents dripping from the nozzle.

The velocity of the aerosol plume generated by the nozzle is reduced as the aerosol passes through a chamber. The chamber contains an axial counterflow tube through which a precisely regulated gas flow opposes the velocity of the aerosol emanating from the nozzle. The control of this counter-flow gas finely controls the arrest of the nozzle exit plume, as well as stops gas flow during expiration, thereby minimizing the use of heliox during expiration. This virtual baffling phenomenon reduces the aerosol velocity and results in a uniformly distributed aerosol plume, and enables an aerosol output greater than 70% of the aerosol generated by the nozzle. Absence of a counterflow gas results in aerosol losses due to high velocity deposition on the sidewalls of converging cone. In one embodiment, the nozzle and counterflow tube have a common port and receive gas meted from valve V2. In another embodiment, the counterflow tube has an independent gas source, and receives gas at pressure P3 regulated by regulator R3. The gas flow from the counterflow tube is switched on or off independently using a dedicated fast switching solenoid valve. Typically, the onset of the counterflow is activated prior to activating the aerosol generation through the nozzle and deactivated following generation of aerosol from the nozzle More specifically, a 3-2-way solenoid valve V3 interchanges the gas flow on or off 50 ms before and after the aerosol is switched on or off, respectively. This procedure is performed to conserve the amount of gas required for aerosolization and to control the total output flow rate from the system. In one embodiment of the invention, the counterflow tube control and gas supply can be made independent by having a common gas port for both the nozzle and the counterflow tube. This further simplifies the pneumatic liquid aerosol system by eliminating R3 and V3.

The slowed aerosol generated within the chamber may then be focused using a delivery cone, which may be fitted to the chamber using a lip seal or other sealing mechanism that mates with the chamber exterior wall of the chamber. The length of the cone and internal shape are optimized to minimize wall deposition of the aerosol and to provide a soft aerosol exiting the output cone. The cone output port tip is designed to connect with other AeroPulsR related complementary aerosol delivery devices.

The combination of the aerosol chamber and delivery cone forms the shape of a pod, which rests on a pedestal. Aerosol that is deposited on the sidewalls of the chamber and cone may drain through a drain hole into a condensation collection well built into a pedestal. The combination of the chamber and delivery cone is able to house the nozzle, counterflow tube and the aerosol before delivery in a compact manner with minimum losses of aerosol. The chamber may include two ribs that match with two matching notches on the pedestal to allow for easy installation and removal. This allows the user to disassemble the elements within the chamber and cone for cleaning and maintenance.

In another embodiment, the AeroPulsR system may be configured to deliver aerosols on-demand, for which several of the system's capabilities are not required. In this embodiment, the vial may be charged with a prescribed dose volume and mounted onto the console. Similar to generic atomizers, the system may include a wye piece comprising a mouthpiece and exhalation valve along with an exhaust filter. The aerosol generation may for instance be set at a dose rate between 0.1 and 5 ml/minute, i.e. up to 10 times greater than alternative aerosol generation delivery devices. A dose rate of 0.3 ml/min is typical for atomizers used to output aerosol diameters of 3 μm median mass aerodynamic diameter (MMAD), whereas the AeroPulsR system allows 3 ml/min or more to be inhaled through the mouthpiece. Upon activating the AeroPulsR system, the patient breathes until the dose of the liquid in the vial is depleted. This allows the medicine delivery time to be reduced to 1/10th of the delivery time of a generic atomizer.

In a preferred embodiment, the AeroPulsR system may be configured to deliver aerosol with a pressure assist. This enables expansion of the patient's lung and airways volumes to improve aerosol drug penetration and deposition. In one embodiment, a bidirectional valve may be attached directly to a cone. In another embodiment, the bidirectional valve may be connected to the cone via a wye, wherein the wye may include a filter and a pressure release valve. The bidirectional valve assembly comprises an aerosol inlet, an aerosol outlet, and an aspiration port. During inhalation, the bidirectional valve allows the aerosol to enter through the inlet and pass through an aerosol delivery channel port to the patient, while the bidirectional valve concurrently occludes the aspiration port. The patient's inspiratory volume is governed by the gas pressure of the aerosol in the chamber and cone. During exhalation, the bidirectional valve opens the aspiration port, while occluding the aerosol delivery channel port. The opening of the aspiration port enables the patient to exhale through a very low resistance. Simultaneously, to vent the pressure generated inside the chamber-cone, the excess pressure is vented through a pressure relief valve, which may be set or adjustable. In a preferred embodiment, the bidirectional valve assembly comprises a flap valve operated pneumatically through a 5-2-way solenoid valve V4 in the console.

Notably, there are no electrically conducting wires near the patient. Using pressure P regulated by the primary regulator R, the 5-2-way valve V4 may switch the direction of pressure, resulting in a 90 degree angular motion of the bidirectional valve. When the aerosol is generated for inspiration, a corresponding control signal is transmitted to the 5-2-way valve V4 to switch the pressure. This procedure results in a 90° rotation of the bidirectional flap valve, thereby opening the aerosol delivery channel port so that aerosol may be delivered to the patient. The rotation of the bidirectional flap valve simultaneously closes the aspiration port. When the 5-2-way valve V4 switches the pressure to an alternate position, the bidirectional flap valve closes the aerosol passage, while simultaneously opening the exhaust port, thereby facilitating exhalation by the patient.

In one embodiment, the nozzle may include a 500 μm diameter exit orifice and a gas flowrate of 30 L/min. Aerosol may be generated and delivered either continuously or in defined boluses during inspiration. This functionality is achieved by the synchronous activation and deactivation of aerosol generation dictated by the nozzle and the bidirectional valve. As discussed, aerosol may be generated or arrested in the nozzle by controlling the pressure in the aerosolization space within the nozzle. The aerosol velocity may be reduced in the chamber and cone by a counterflow tube. Subsequently, the bidirectional valve may delay the aerosol's delivery times, as necessary. To deliver aerosol pulses between 50 ml and 2 L, the liquid aerosol generation pulse duration may be selectable between 100 ms and 4 s, respectively. The final aerosol inspiratory and expiratory breaths by the patient are synchronized by the bidirectional valve.

Tidal volume for inspiration and periodic breath rate are determined according to the size of the patient. To increase the drug concentration while retaining the tidal volume, an aerosol concentrator may be placed in between the cone and the bidirectional valve. The cone, concentrator and bidirectional valves maybe configured to be easily interconnected or disconnected, but with connections sufficiently secure to prevent leakages. The volume of the aerosol is dependent on the volume of the aerosol chamber as well as additional gas from the counterflow tube. These parameters control the dilution of the overall aerosol concentration. An aerosol concentrator may be incorporated to reduce the volume of the gas. The concentrator may comprise accelerating/converging slits and decelerating/diverging slits separated by 1.5 mm gap.

Due to their momentum, the higher inertial aerosol particles (2-5 μm in size) pass though the slits and through the gap into the deccelerating slits, whereas lighter particles and dilution gas (<1 μm in size) escape through the sides of the gap and exit through the exhaust port in the concentrator. By having the dilution gas and other non-aerosol particles escape through the exhaust port, a high concentration of aerosols is outputted. The concentrator reduces gas flow to the patient by ⅕th of the initial flow (i.e., 6 l/min) while maintaining the same mass of the aerosolized drug. This procedure may increase the drug concentration up to five-fold.

DETAILED DESCRIPTION OF THE DRAWINGS

Figure 1:
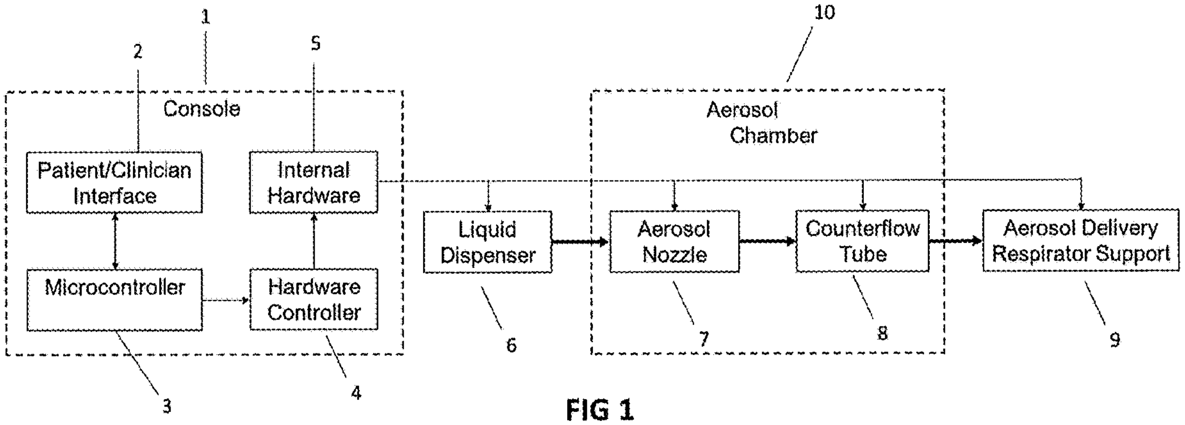
FIG. 1 is a block diagram of the components of the aerosol generation device.

FIG. 1 is a block diagram schematically demonstrating the components of the aerosol generation device. The invention comprises a console 1 and its components which interact with the patient/clinician via a patient/clinician interface 2 to deliver precise doses of aqueous aerosols as shown in FIG. 1. The console 1 may comprise the patient/clinician interface 2, microcontroller 3, hardware controller 4 and internal hardware 5. Several components, including the liquid dispenser 6, aerosol nozzle 7, counterflow tube 8 and the aerosol delivery respiratory support 9, are pneumatically controlled by the hardware controller 4 which comprises solenoid valves that are triggered by the microcontroller 3. The settings for the microcontroller 3 and internal hardware 5 may be set in accordance with a prescribed dosage. When the patient/clinician initiates the therapy via the patient/clinician interface 2, the microcontroller 3 interacts with the hardware controller 4 to effect aerosol output. The aerosol chamber 10 comprises the aerosol nozzle 7 and the counterflow tube 8, both of which are housed therein. The aerosol chamber 10 is configured to focus the aerosol generated by the nozzle 7 downstream. The aerosol delivery respiratory support 9 enables delivery of the aerosol to the patient, and ensures aerosol is only delivered during inhalation.

Figure 2:
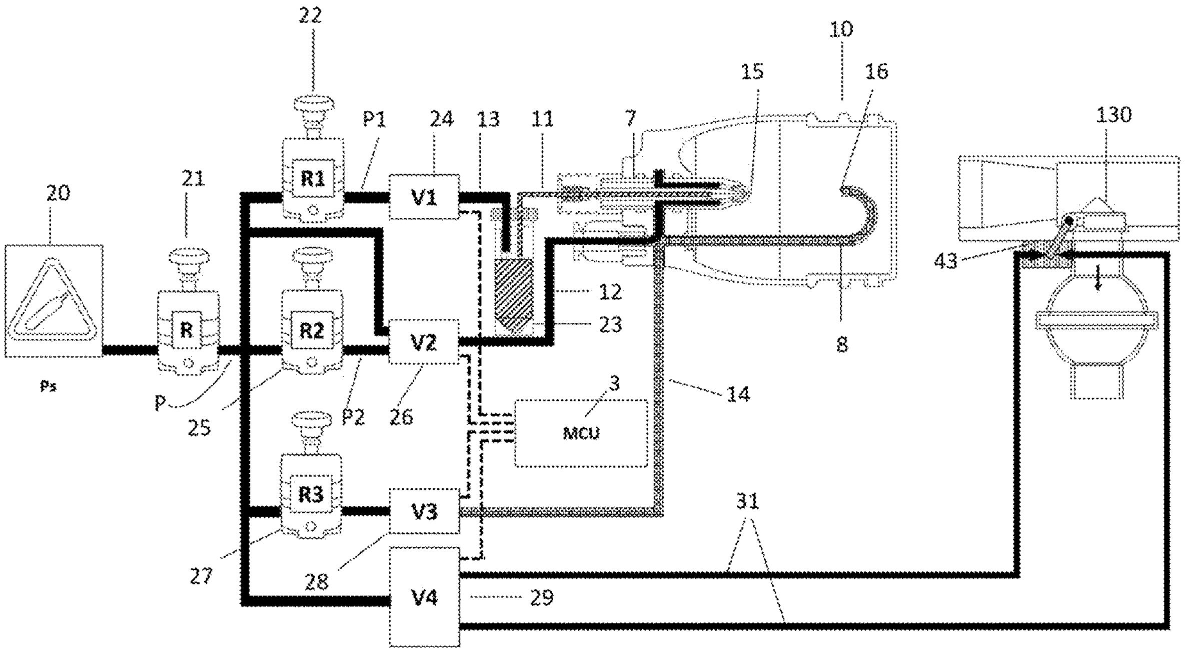
FIG. 2 is a schematic diagram of the pneumatic system and aerosol generation device.

FIG. 2 schematically shows the system according to the invention. Compressed air or heliox is supplied to the system by a high-pressure source 20, and regulated by a system pressure regulator 21, which is connected in series with the high-pressure source 20. This stable and regulated pressure is then distributed downstream to the constituent systems through a gas supply line network.

Pressure may be routed to a liquid vial 23 through a gas supply line 13, along which a liquid pressure regulator 22 and a 3-2-way solenoid valve 24 are disposed. The liquid pressure regulator 22 may be configured to pressurize the liquid vial 23, which supplies liquid to the aerosol nozzle 7 via a liquid supply line 11. A 3-2-way solenoid valve V1 24 may be disposed between the liquid pressure regulator 22 and the liquid vial 23 to control the flow of liquid from the liquid vial 23 to the nozzle liquid input 60 of the nozzle 7. In a preferred embodiment, the 3/2-way solenoid valve 24 is by default in a closed position, and prior to aerosolization may switch to an open position, thereby turning the pressure on.

The system may additionally include a three-way solenoid valve 26 configured to control the flow of liquid within the liquid microchannel 70 inside the nozzle barrel 66. Regulated pressures from the system pressure regulator 21 and a nozzle gas regulator 25 are routed through the three-way solenoid valve 26. The pressures P, P1 and P2 respectively corresponding to the system regulator R 21, liquid pressure regulator R1 22 and nozzle gas regulator R2 25, are adjusted such that P>P1>P2. When the V2 26 is open to pressure P from regulator R 21, the pressurized liquid flow in the aerosol nozzle 7 is arrested. However, when the V2 26 is open to pressure P2 from regulator R2 25, the liquid flows through the aerosol nozzle 7 for aerosolization.

Pressure may be routed to counterflow tube 8 via a counterflow gas tube supply line 14 and expelled out of a counterflow gas tube exit opening 16. A counterflow tube regulator 27 may be included to control the gas pressure in the counterflow tube 8. A second 3-2-way solenoid valve 28 may be included intermediate to the counterflow tube regulator R3 27 and counterflow tube 8. When in its default closed position, the 3-2-way solenoid valve 28 allows for independent control of the counterflow tube 8.

A 5/2-way solenoid valve V4 29 may be included to control the pressure output to the aerosol delivery respiratory support 9, which comprises a bidirectional valve assembly 130. Two pneumatic lines 31 extend between the 5/2-way solenoid valve 29 and a pneumatic actuator 43 located at the bidirectional valve assembly 130. Pressure regulated by the system pressure regulator 21 may be switched between the two pneumatic lines 31 in order to open and close the aerosol delivery channel port 136 of the bidirectional valve assembly 130, thereby controlling whether the aerosol output to the patient is allowed or arrested.

Figure 3:
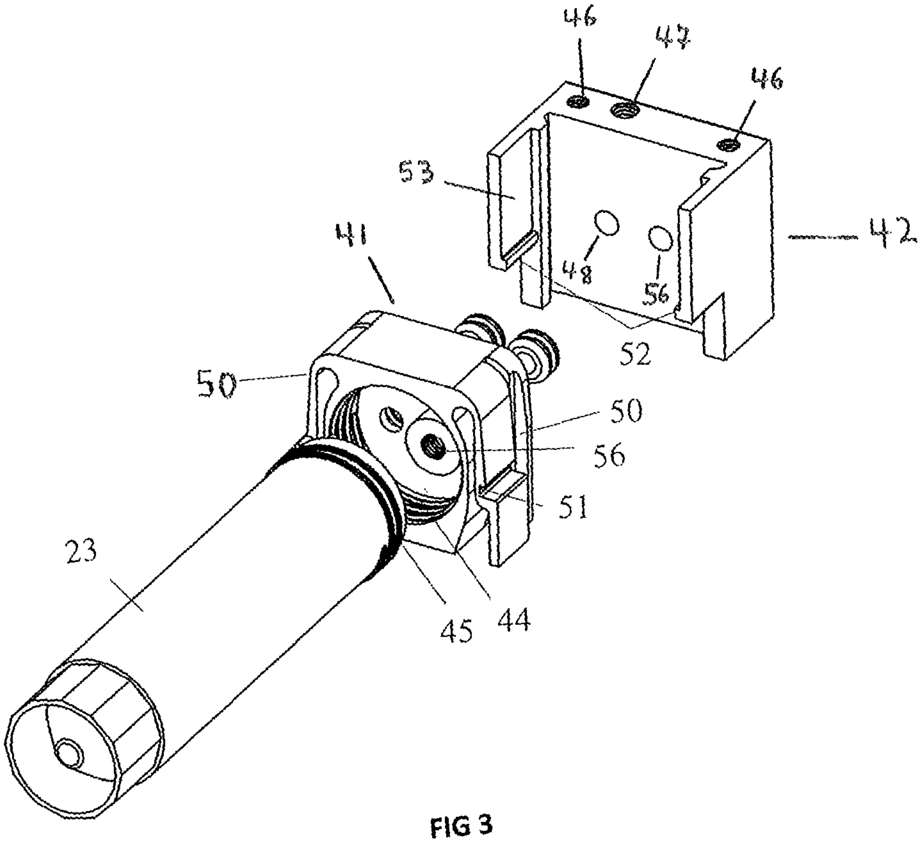
FIG. 3 shows an exploded view of the liquid dispenser system.
Figure 4A:
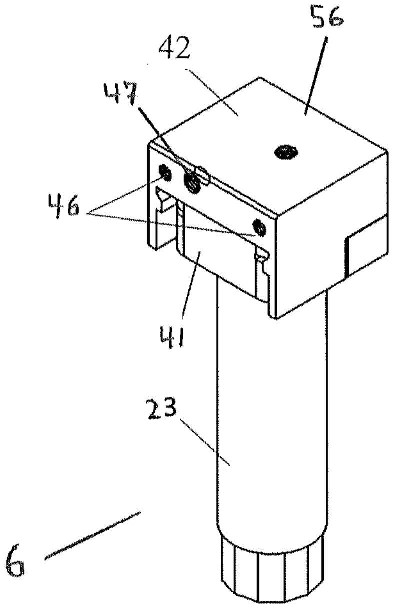
FIG. 4A shows the assembled perspective view of the dispenser system.
Figure 4B:
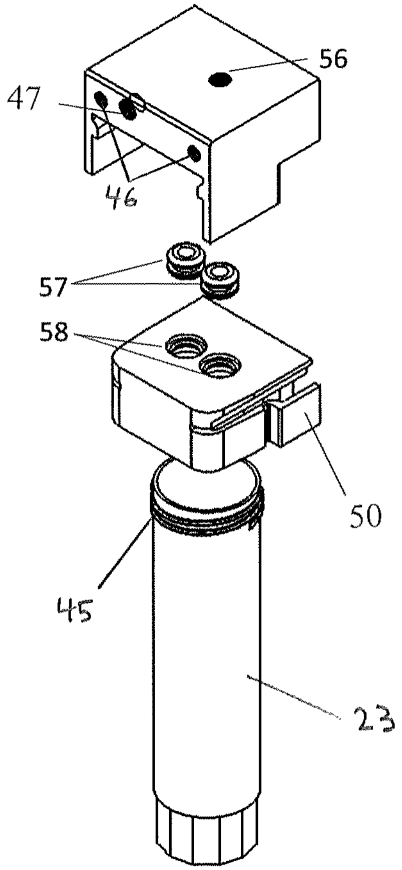
FIG. 4B shows an alternate exploded view of the dispenser system as shown in FIG. 3

FIGS. 3-5 show various views of the liquid dispenser 6, which supplies liquid drug to the nozzle 7. A liquid vial 23 is screwed into the dispenser cap 41, and then is slid into the dispenser mount 42. In a preferred embodiment, the liquid vial 23 may contain standard liquid volumes such as 15 mL or 50 mL, but the volume of the vial 23 may be any volume suitable for a given dosage or usage. The vial 23 may include half turn threads 45 configured to mate with cut threads 44 on the dispenser cap 41. This configuration promotes easy loading by achieving coupling with only a half twist of the vial 23.

Figure 5A:
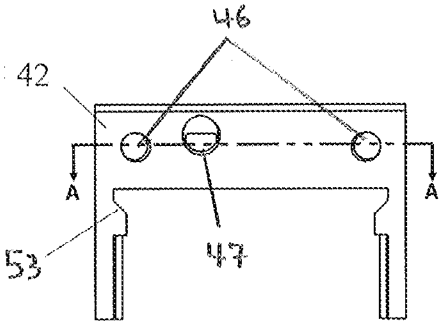
FIG. 5A shows the side view of the dispenser cap.
Figure 5C:
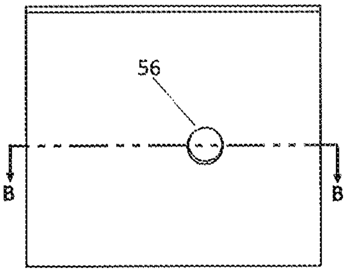
FIG. 5C shows the top view of the dispenser cap.
Figure 5B:
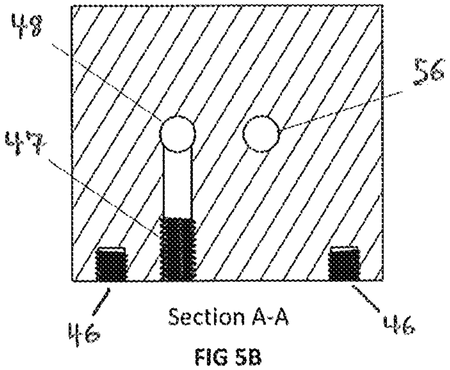
FIG. 5B shows the longitudinal section denoted A-A in FIG. 5A.
Figure 5D:
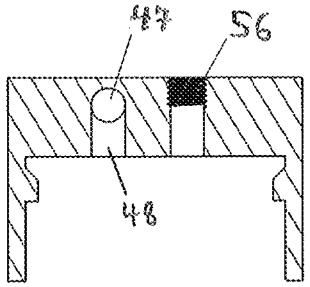
FIG. 5D shows the vertical section denoted B-B in FIG. 5C.

The dispenser mount 42 may include a front recess through which the dispenser cap 41 is inserted, a back wall opposite the front recess, a top surface, and two side walls. The back wall of the dispenser mount 42 may include two threaded holes 46 for mounting the dispenser assembly onto the console 1. The liquid vial 23 is pressurized through a threaded port 47 located between the two threaded holes 46 on the back wall of the dispenser mount 42. The threaded port 47 extends to a perpendicular hollow channel 48 inside the dispenser mount 42 that directs the compressed gas downwards into the vial 23 (FIG. 5B). As shown in FIGS. 5B and 5D, a through channel 56 is included on the top surface of the dispenser mount 42. The through channel 56 includes threads for connecting the nozzle 7 to the dispenser mount 42 via a male luer lock fitting and a capillary. The dispenser cap 41 may include a locking mechanism comprising two cantilever clips 50 with slots 51 configured to interface with corresponding keys 52 located on sliding tracks 53 in the interior side walls of the dispenser mount 42. Each of the cantilevers 50 may include a ramped section such that the cantilevers 50 must be pinched to fit onto the sliding tracks 53 when inserting the dispenser cap 41 into the dispenser mount 42. When the dispenser cap 41 is fully inserted into the dispenser mount 42, the keys 52 on the dispenser mount 42 fall into the slots 51 of cantilevers 50, thereby creating a secure connection between the dispenser cap 41 and dispenser mount 42. Two O-rings 57 may be included in the liquid delivery port 58 to create an air and fluid tight seal when the dispenser cap 41 is slid into the dispenser mount 42. Additionally, the sliding tracks 53 on the dispenser mount 42 may be configured such that the O-rings 57 are compressed when the dispenser cap 41 is inserted into the dispenser mount 42. A capillary section and an inline check valve may be threaded to the liquid delivery port 58 on the dispenser cap 41.

Figure 6A:
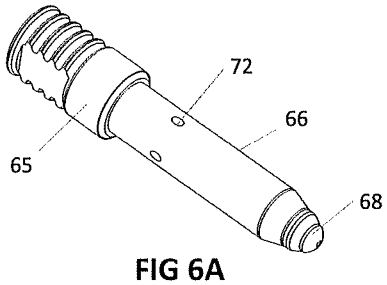
FIG. 6A shows a perspective view of the nozzle.
Figure 6B:
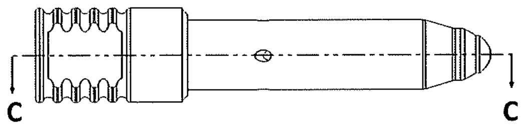
FIG. 6B shows the side view of the nozzle.
Figure 6C:
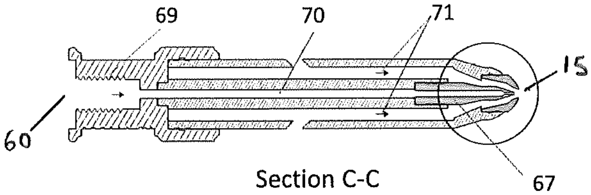
FIG. 6C shows the sectional view denoted C-C in FIG. 6B.
Figure 6D:
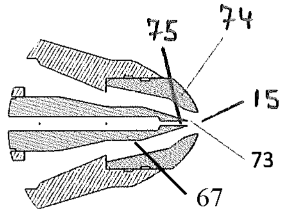
FIG. 6D shows a detailed view of the section C-C showed in FIG. 6C.

FIG. 6 shows the structural components of the nozzle 7, which may include a knob 65, barrel 66, liquid jet nozzle tip 67 and nozzle cap 68 (FIG. 6A). Nozzle 7 includes a nozzle liquid input 60, a nozzle gas input, and an aerosol exit orifice 15. The liquid is fed from the liquid vial 23 to the nozzle liquid input 60 via a liquid supply line 11, which may for instance be a capillary. In a preferred embodiment, the knob 65 may include threads 69 to allow a capillary to be connected to the nozzle 7 via a male luer connector. The liquid may then be fed through a liquid microchannel 70 running axially through the lengthwise axis of the nozzle barrel 66 between the nozzle liquid input 60 and the fluid exit 75, as shown in section view C-C FIG. 6C. Gas flows to the nozzle gas input via a gas supply line 12, and is fed to a plurality of air microchannels 71, which may be disposed coaxial to the liquid microchannel 70. In a preferred embodiment, four air microchannels 71 are included inside the nozzle 7. Each air microchannel 71 may have a corresponding hole 72 in the nozzle barrel 66 through which the gas may flow in. The gas exit 74 of the air microchannels 71 and fluid exit 75 of the liquid microchannel 70 converge at the aerosolization space 73 where the aerosolization occurs. The aerosolizing space 73 is defined between the outlet of the liquid jet nozzle tip 67 and the nozzle cap 68 (FIG. 6D). The aerosols generated in the aerosolization space 73 are expelled through the aerosol exit orifice 15 into the aerosol chamber 10.

Figure 7A:
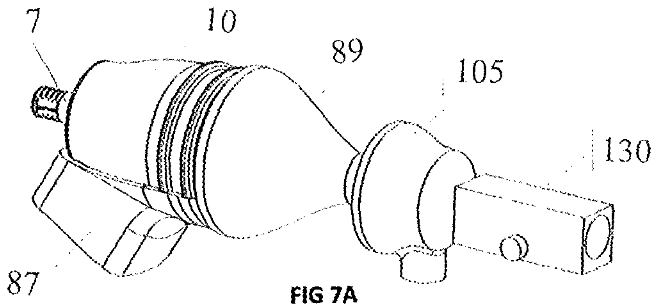
FIG. 7A shows a perspective view of an assembly comprising a nozzle, aerosol chamber, counter flow tube, chamber pedestal, aerosol concentrator and flapper block.
Figure 7B:
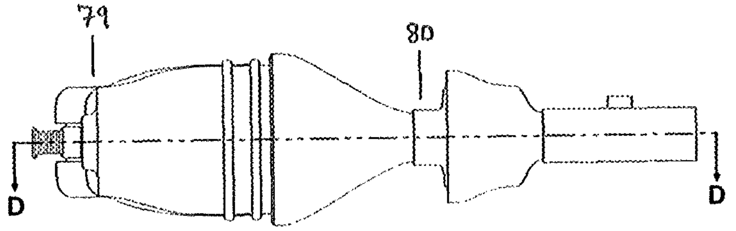
FIG. 7B shows the top view of assembly in FIG. 7A.

FIG. 7 shows an assembly including a chamber, cone, concentrator, and bidirectional valve. This assembly comprises a nozzle 7, a pedestal 87, an aerosol chamber 10, a cone 89, a concentrator 105, and a bidirectional valve assembly 130. The aerosol chamber 10 comprises an aerosol chamber input end 79 and an aerosol chamber output end 80. The aerosol chamber 10 houses the nozzle 7 and the counterflow tube 8. The nozzle 7 is inserted from the backside of the chamber 10. In a preferred embodiment, the chamber 10 may additionally include a cone 89 having a cone input end 93 having larger diameter and a cone output end 94 having a smaller diameter. The cone input end 93 may connect with the aerosol chamber output end 80, and the cone output end 94 may connect with the concentrator input end 117. In this configuration, the aerosol chamber 10 is effectively extended such that the aerosol chamber output end 80 and cone output end 94 are one and the same. In another embodiment, the chamber 10 and concentrator 105 may be configured to allow the aerosol chamber output end 80 to directly connect to the concentrator input end 117. The aerosol chamber 10 may include three annuli surrounding the nozzle barrel 66, specifically a first O-ring annulus 81, an air annulus 82, and a second O-ring annulus 83. The air annulus 82 supplies air to the air microchannels 71 in the nozzle barrel 66. The first and second O-ring annuli 81, 83 are disposed on opposite sides of the air annulus 82, and house O-rings.

Figure 7C:
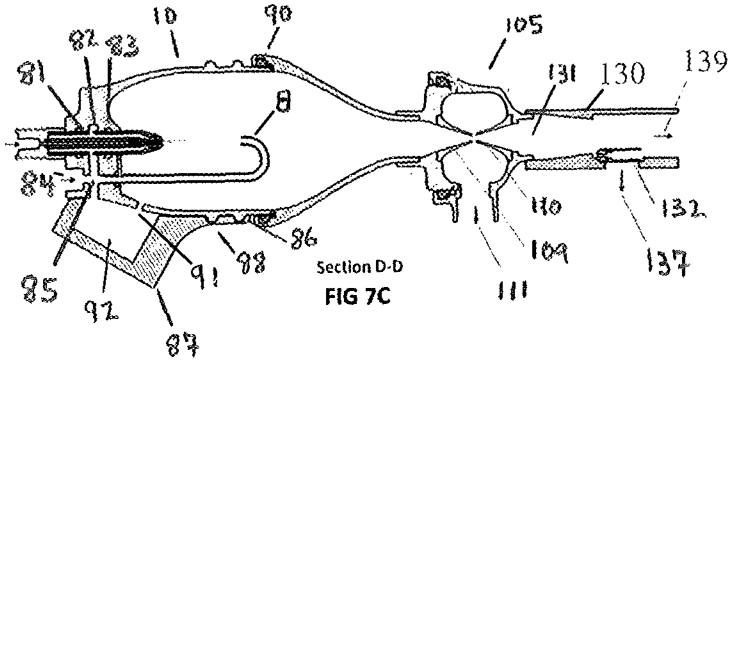
FIG. 7C shows the sectional view denoted D-D in FIG. 7B.

In one configuration (as shown in FIG. 7C), a female pneumatic quick connect is threaded on the back of the chamber 10 for supplying air to the nozzle 7 and the counterflow tube 8 through a common port 84. The access hole 85 for the air annulus 82 for nozzle 7 may be plugged using a grub screw. In an alternate configuration (as shown in FIG. 2), the counterflow tube 8 and the nozzle 7 may have independent sources of compressed air supply, and accordingly include separate ports. The compressed air may be supplied using respective male quick connect pneumatic connectors for the nozzle 7 and the counterflow tube 8. The access hole 85 for the air annulus 82 may be plugged using a grub screw. The chamber 10 may further comprise two or more ribs 86 configured to mount the chamber 10 onto a pedestal 87. The pedestal 87 may include matching slots 88 configured to interface with the ribs 86. The structure of the pedestal 87 and its slots 88 are structured to enable the chamber 10 to firmly click onto the pedestal 87 for easy mounting and dismounting. For focusing the generated aerosol, a cone 89 may optionally be attached to the aerosol chamber output end 80 via a lip seal 90. The chamber 10 may further include a small drain hole 91 located at the bottom of the chamber 10 for draining liquid deposited on the inside walls of the chamber 10 and/or cone 89. Liquid draining through the small drain hole 91 may be deposited into an inbuilt reservoir 92 located in the pedestal 87. The gas flow from the counterflow tube 8 opposes and reduces aerosol velocity emanating from the nozzle 7, thereby creating a virtual baffle. Disposed downstream from the aerosol chamber 10 is concentrator 105 including an input tube 109, an output tube 110, and an exhaust port 111. Downstream of the concentrator 105 is the bidirectional valve assembly 130 including the bidirectional valve assembly input 131, bidirectional valve assembly output 139, aspiration port 137 which is shown in FIG. 7C in a closed configuration blocked by cylindrical disc 132.

FIG. 8 shows a concentrator have a cross-slit, in the following named a cross concentrator 105 shown in FIG. 8A, which comprises an input housing part 106 and an output housing part 107. The input housing part 106 comprises a patterned mold 108 configured to connect with an input tube 109. Similarly, the output housing part 107 is configured to connect with an output tube 110. The input tube 109 may include an input tube entrance port 119, for instance having a circular cross-section as in the shown embodiment, but could alternatively square, polygonal, oval or of any other suitable shape, and an input tube exit port 120 having the shape of a cross-slit, wherein the cross-sectional shape of the input tube 109 transitions from said non-cross-slit-shape at the input tube entrance port 119 to a cross-slit-shape at the input tube exit port 120. The cross-slit shape preferably includes two linear slots crossing each other at a 90° angle, but alternative any other angle is possible. Also, the crossing slits do not necessarily need to be linear, although this is a preferred shape from both a manufacturing standpoint as well as an alignment standpoint with a corresponding output tube cross-slit. The output tube 110 may include an output tube entrance port 121 and an output tube exit port 122, wherein the cross-sectional shape of the output tube 110 transitions between the output tube entrance port 121 and an output tube exit port 122. The output tube entrance port may have a cross-slit-shape corresponding to the cross-slit of the input tube, and may be aligned therewith. As shown in FIG. 8D, the input tube 109 may converge from the input tube entrance port 119 to the input tube exit port 120, such that the input tube entrance port 119 has a greater cross-sectional area than that of the input tube exit port 120. Conversely, the output tube 110 may diverge from the output tube entrance port 121 to the output tube exit port 122, such that the output tube entrance port 121 has a lesser cross-sectional area than that of the output tube exit port 122. The input tube exit port 120 and output tube entrance port 121 may be disposed along a joint longitudinal axis and spaced apart by a gap 123.

Diverging of the input tube is optional but may be preferred for increasing the aerosol velocity through the cross-slit and therefore the momentum of the aerosol particles, resulting in a higher particle concentration rate. Converging of the output tube is likewise optional but preferred for reducing the velocity of the aerosol flow for a smoother for inhalation action and distribution of the aerosol particles. In lieu of converging/diverging profiles within the input/output tubes, a similar effect could also be accomplished by including additional components with similar profiles connected upstream/downstream of the input/output tubes. In this context, converging is to be understood as reducing the total cross-section of the lumen in the input tube along the direction of aerosol flow, while diverging is to be understood as increasing the total cross-section of the lumen in the output tube along with the direction of flow.

Figure 8A:
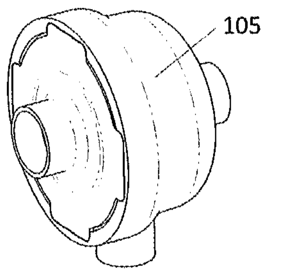
FIG. 8A shows an assembled perspective view of the aerosol concentrator.
Figure 8C:
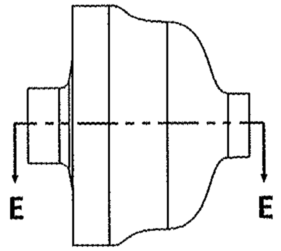
FIG. 8C shows the assembled side view of the aerosol concentrator.
Figure 8B:
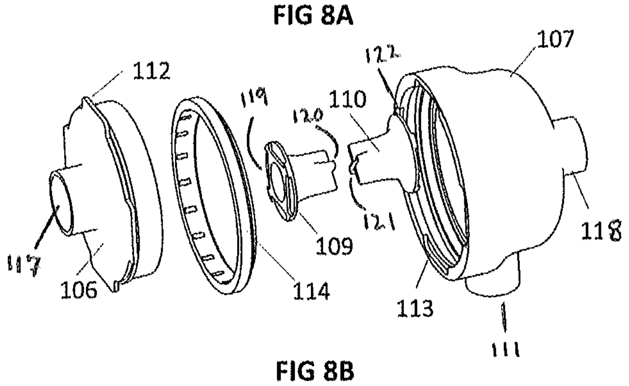
FIG. 8B shows an exploded view of the aerosol concentrator.
Figure 8D:
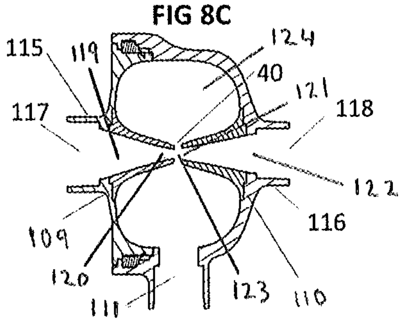
FIG. 8D shows the sectional view denoted E-E in FIG. 8C.

FIG. 8B shows the exploded view of the concentrator assembly. The output housing part 107 may include an exhaust port 111 for venting dilution gas. The housing 106, 107 may share a joint longitudinal axis with the input tube 109 and the output tube 110. This longitudinal axis is also the axis of the aerosol flow and runs through the center of the cross-slit, which is the point of intersection of the linear slits. The plenum 124 may be substantially encompassed by either the input housing part 106 or the output housing part 107.

The housing part not encompassing the plenum 124 may be essentially disc-shaped, whereas the housing part substantially encompassing the plenum 124 may also include the exhaust tube 111 extending essentially radially in a transverse direction with respect to said longitudinal axis. The input tube 109 and output tube 110 may have radial sizes transverse to the longitudinal axis that are less than a third of a radial size of the plenum 124 transverse to said longitudinal axis. The exhaust port 111 may be oriented perpendicular to the longitudinal axis of aerosol flow between the concentrator input end 117 and concentrator output end 118, as also defined by the cross-section E-E shown in FIG. 8C. A pressure relief valve may be connected to the exhaust tube 111 for keeping a constant pressure within and across the concentrator 105, including at the output tube exit port 122. Both the input housing part 106 and the output housing part 107 may include lobes 112 and corresponding lobe molds 113 for alignment. The input housing part 106 and the output housing part 107 may be connected via a lip seal 114. The housing 106, 107 may encompass a plenum 124 defined by a void space surrounding and encompassing the input tube 109 and output tube 110, preferably in the shape of an annulus but alternatively could be any other shape that creates sufficient space around the gap 123 for receiving the exhaust aerosol of low particle concentration without significant pressure drop, such that the overall pressure drop through the concentrator, and therefore for the entire system, is kept low. The plenum 124 may be connected to the exhaust port 111. The concentrator assembly may include a concentrator input mating surface 115 and a concentrator output mating surface 116 (shown in FIG. 8D) respectively corresponding to the concentrator input end 117 and the concentrator output end 118 through which the respirable aerosol flows. The concentrator input mating surface 115 may be configured to facilitate easy attachment with the cone 89 without necessitating fasteners.

Figure 9A:
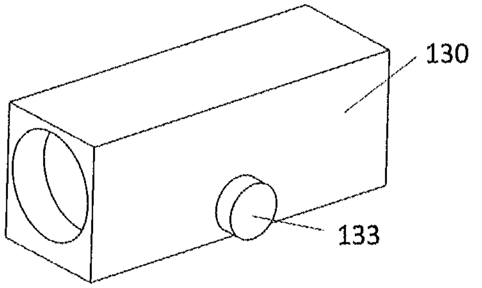
FIG. 9A shows a perspective view of the flapper block.
Figure 9C:
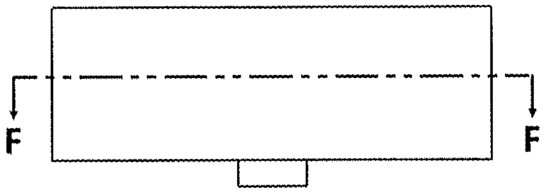
FIG. 9C shows the top view of the flapper block.
Figure 9B:
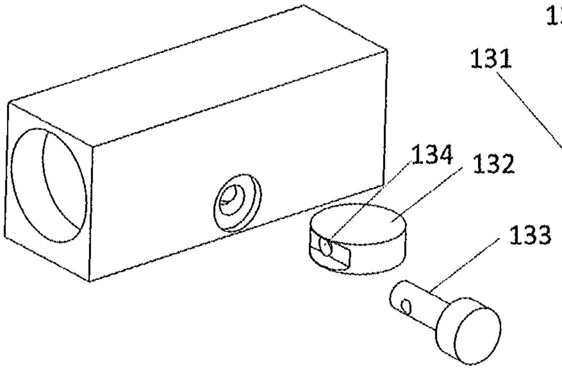
FIG. 9B shows an exploded view of the flapper block.
Figure 9D:
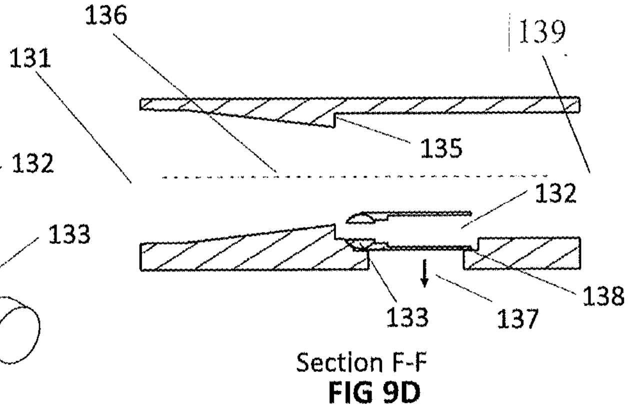
FIG. 9D shows the sectional view denoted F-F in FIG. 9C.

FIG. 9 shows an Aerosol delivery respiratory support assembly comprising the bidirectional valve assembly 130 shown in FIG. 9A enables functionality of the aerosol delivery respirator support 9. In one embodiment, the bidirectional valve assembly input 131 may connect with the cone output end 94 of the cone 89. In another embodiment the system includes a concentrator 105, the bidirectional valve assembly input 131 may connect with the concentrator output end 118 of the concentrator 105. A cylindrical disc 132 is included inside the bidirectional valve assembly 130. A pivot pin 133 is inserted through a hole in a sidewall of the bidirectional valve assembly 130 and connects to the disc 132 by interfacing with a set screw 134 located on the disc 132. These elements and their interactions are shown in an exploded view in FIG. 9B. As seen in FIG. 9D, the bidirectional valve assembly 130 includes an annular aerosol delivery channel port 136 extending between a bidirectional valve assembly input 131 and a bidirectional valve assembly output 139. The upper wall of the aerosol delivery channel port 136 includes a first seat 135 against which the disc 132 butts up against when in a vertical position, thereby inhibiting further counterclockwise rotation. The lower wall includes a second seat 138 offset a distance from the pin 133 such that the disc 132 is simply supported when in a horizontal position, as shown in FIG. 9D. The pin 133 may be actuated using a reciprocating pneumatic actuator 43 driven by the 5/2-way solenoid valve 29. When actuated by the pneumatic actuator 43, the pin 133 may rotate the disc 132 90 degrees to switch between open and closed positions. FIG. 9D shows the bidirectional valve assembly in an open position, wherein the disk 132 seats horizontally within the second seat 138 such that the aerosol delivery channel port 136 is open and the aspiration port 137 is closed. In a closed position, the disc 132 seats vertically within the first seat 135 such that the aerosol delivery channel port 136 is blocked and the aspiration port 137 is opened. In one embodiment of the invention, the bidirectional valve assembly output 139 may be configured to attach to an endotracheal tube (not pictured) for remote aerosol delivery.

FIGS. 10-14 demonstrate some results achieved by the system according to the invention with respect to the particle size distribution over the liquid flow rate of the liquid to be aerosolized, showing graphs for viscosities of 4 cP, 11 cP and 21 cP for the aerosolized liquid for a variety of nozzles of different nozzle exit orifice diameters, aerosolizing gases and system pressures.

Figure 10:
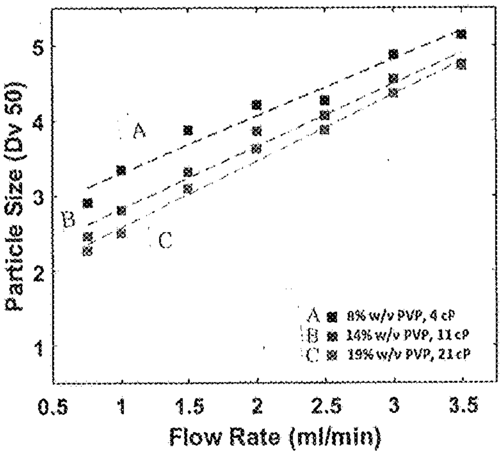
FIG. 10 shows a plot of particle size versus flow rate for PVP solutions of different viscosities aerosolized using compressed air and a 500 μm orifice nozzle.

FIG. 10 shows plots of flow rate (ranging from 0.75 ml/min to 3.5 ml/min) versus particle size (Dv 50 in units of μm) for three different concentrations of aqueous polyvinylprrolidone (PVP) with a system using compressed air, a system pressure of 60 psi, and a nozzle exit orifice diameter of 500 μm. The three different concentrations (by weight) of aqueous PVP solutions were 8%, 14% and 19%, and resulted in respective solution viscosities of 4, 11 and 21 cP. The 8% concentration solution is denoted by square plot points with a solid trendline, the 14% concentration solution is denoted by circular plot points with a dashed trendline, and the 19% concentration solution is denoted by triangular plot points with a dotted trendline. When the PVP solutions were aerosolized by AeroPulsR system at liquid pressure of 60 psi, the particle sizes of aerosols were found to be related to (i) PVP concentrations, (ii) the flow rates of the liquids, and (iii) the type of compressed gas used. From the flow rate ranging from 0.75 ml/min to 3.5 ml/min for each solution, the majority of the Dv 50 values of the aerosols were under 5 μm, except in one test where 8% PVP solution was aerosolized at 3.5 ml/min and compressed air was used. Meanwhile, smaller aerosols were obtained from a solution with higher PVP concentrations at the same flow rate.

Figure 11:
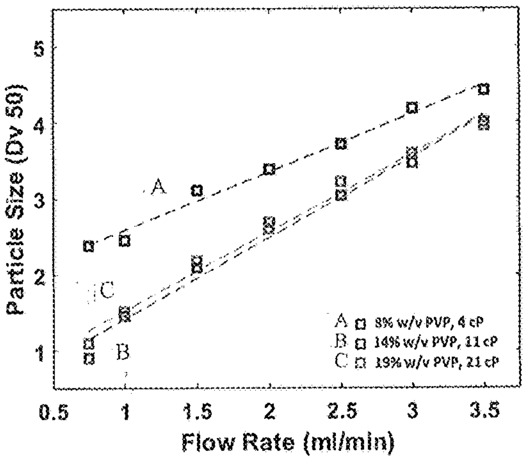
FIG. 11 shows a plot of particle size versus flow rate for PVP solutions of different viscosities aerosolized using compressed heliox and a 500 μm orifice nozzle.

FIG. 11 shows a plot for the same parameters as in FIG. 10, except substituting compressed heliox (a mixture of 80% helium and 20% oxygen) for compressed air to investigate the effect of compressed heliox on the particle size. Accordingly, aerosolization is conducted with identical settings mentioned previously with compressed air. A notable decrease in the particle sizes is observed with compressed heliox, when compared with compressed air.

Figure 12:
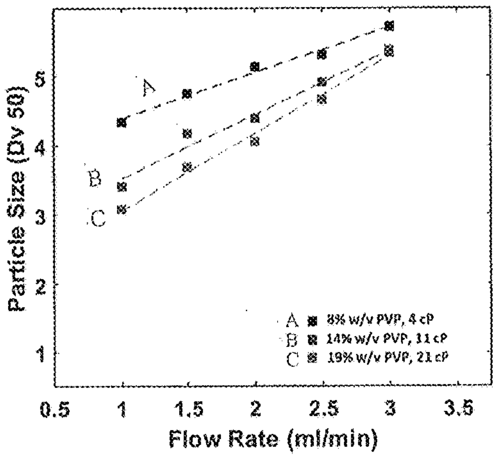
FIG. 12 shows a plot of particle size versus flow rate for PVP solutions of different viscosities aerosolized at a lowered pressure using compressed air and a 500 μm orifice nozzle.

FIG. 12 shows a plot for substantially the same parameters as in FIG. 10, except at a reduced system pressure of 50 psi. For obtaining this plot, the liquid pressure was reduced to 49 psi from 60 psi, and the aerosols were measured at a flow rate ranging from of 1 to 3 ml/min for PVP aqueous solution concentration (by weight) of 8%, 14%, and 19%. It was found that the overall aerosol size trend for different PVP solution concentration was similar to that observed for 60 psi liquid pressure. However, particle sizes for individual PVP concentrations were higher when compared with higher gas pressure.

Figure 13:
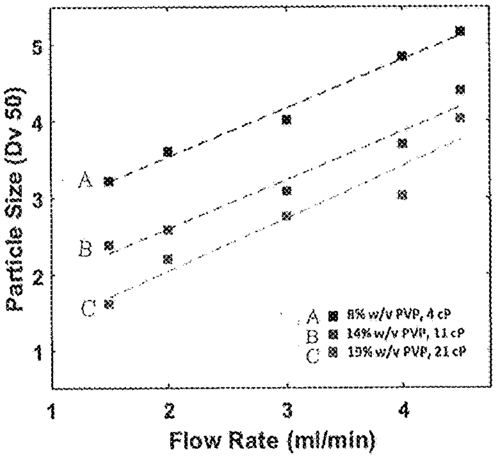
FIG. 13 shows a plot of particle size versus flow rate for PVP solutions with different viscosities are aerosolized using compressed air and a 700 μm orifice nozzle.

FIG. 13 shows a plot for substantially the same parameters as in FIG. 10, except substituting the 500 μm nozzle with a 700 μm nozzle to investigate the size of the nozzle's exit orifice on aerosol particle size. With a system pressure of 60 psi, PVP aqueous solutions with concentrations of 8%, 14%, and 19% were aerosolized with a flow rate ranging from 1.5 to 4.5 ml/min. When compared with aerosol sizes achieved from 500 μm nozzle at 60 psi, it was found that under the same pressure and flow rate conditions, smaller aerosols from the same PVP solution can be generated from the 700 μm nozzle. The size of the nozzle exit orifice, therefore, can be modified to affect the size of the aerosol. For instance, at a flow rate of 3 ml/min, 21 cP PVP solution, and 500 μm nozzle exit orifice diameter, a Dv 50 of 4.2 μm resulted. However, using the same PVP solution with a nozzle exit orifice diameter of 700 μm resulted in a Dv 50 of 2.7 μm.

Figure 14:
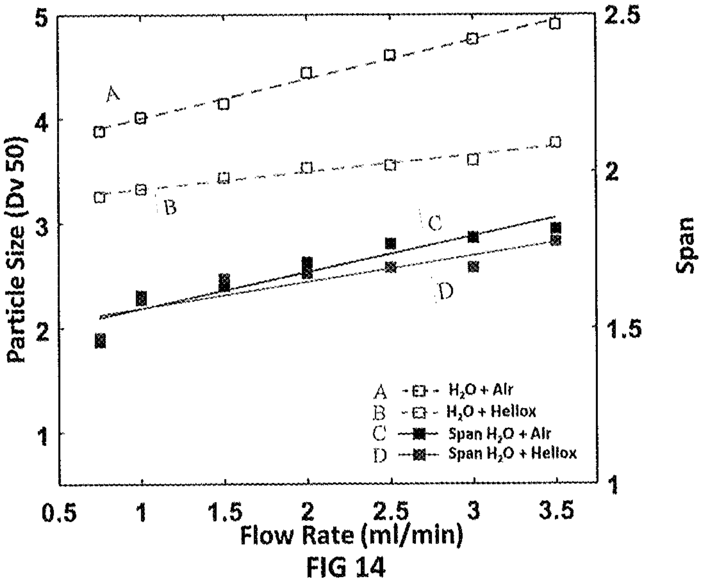
FIG. 14 shows a three-axis plot particle size versus flow rate and particle size versus span, when with a 500 μm orifice nozzle water is (i) aerosolized using compressed air, and (ii) aerosolized using heliox.

FIG. 14 shows a three-axis plot of flow rate (ranging from 0.75 ml/min to 3.5 ml/min) versus particle size (Dv 50 in μm) and span of H2O aerosol versus particle size (Dv 50 in μm) for H2O/compressed air and H2O/heliox. The particle size for the H2O/compressed air combination is denoted by hollow square plot points with a dashed trendline. The particle size for the H2O/heliox combination is denoted by hollow triangular plot points with a dotted trendline. The span for the H2O/compressed air combination is denoted by solid square plot points with a dot-dashed trendline. The span for the H2O/heliox combination is denoted by solid triangular plot points with a solid trendline. The AeroPulsR system generates aerosol particles with a narrow distribution. A narrow span in the range of 1.5 to 2 is observed for both compressed air and heliox.

In the following, additional embodiments are described:

Embodiment 1. An aerosol generating nozzle system for generating a respirable aerosol from a liquid solution or liquid suspension, comprising:

- an aerosol generating nozzle 7 having an aerosol exit orifice 15;
- a fluid source for supplying the liquid solution or liquid suspension to be aerosolized through a liquid supply line 11 to an input 60 of the aerosol generating nozzle 7 at a liquid pressure;
- a first gas supply line 12 connected to gas input of the nozzle 7 for supplying pressurized aerosolizing gas at a pressurized aerosolizing gas pressure to the nozzle 7;
- a first controllable valve 26 for modulating the pressurized aerosolizing gas pressure; and
- a controller 3 connected to the first controllable valve 26 for controlling the same to modulate the pressurized aerosolizing gas pressure; wherein
- the nozzle 7 comprises an internal aerosolizing space 73 connected to at a fluid exit 75 where the liquid solution or liquid suspension enters the aerosolizing space 73 and a pressurized aerosolizing gas exit 74 where the pressurized aerosolizing gas enters the aerosolizing space 73 encompassing the fluid exit 75; wherein
- the controller 3 is configured to modulate the pressurized aerosolizing gas pressure so that a gas pressure of the pressurized aerosolizing gas in the aerosolizing space 73 exceeds and drops below a fluid pressure at the fluid exit 75 in an alternating fashion, wherein an aerosol generation duration is controlled by the time the pressurized aerosolizing gas pressure is kept by the controller 3 below a fluid pressure at the fluid exit 75.

Embodiment 2. The aerosol generating nozzle system according to embodiment 1, wherein the first controllable valve 26 has an input end and an output end and a first adjustable pressure regulator 25 is provided upstream of the input end of first controllable valve 26 for regulating the pressure at the input end of first controllable valve 26 and therefore limiting a maximum pressure at the output end of the first controllable valve 26 when it assumes its fully open configuration.

Embodiment 3. The aerosol generating nozzle system according to embodiment 1 or 2, further comprising a second controllable valve 24 for adjusting the liquid pressure in the liquid supply line 11.

Embodiment 4. The aerosol generating nozzle system according to embodiment 3, wherein the fluid source is a container 23 having an input connected to a second gas supply line 13 and an output connected to the liquid supply line 11 and the second controllable valve 24 is provided in the second gas supply line 13 for modulating a second gas pressure that equals the liquid pressure in the container 23, wherein the controller 3 controls the second controllable valve 24.

Embodiment 5. The aerosol generating nozzle system according to embodiment 3 or 4, wherein the controller 3 is configured to hold the second gas pressure that equals the liquid pressure in the container 23 essentially constant while performing several duty cycles of modulating the pressurized aerosolizing gas pressure so that the gas pressure of the pressurized aerosolizing gas in the aerosolizing space 73 exceeds and drops below in an alternating fashion while maintaining the essentially constant fluid pressure at the fluid exit 75.

Embodiment 6. The aerosol generating nozzle system according to one of embodiments 1-5, wherein a check valve is provided in the liquid supply line 11, preventing a volume flow back from the nozzle 7 towards the fluid source.

Embodiment 7. The aerosol generating nozzle system according to one of embodiments 3-6, wherein the second controllable valve 24 has an input end and an output end and a second adjustable pressure regulator 22 is provided upstream of the input end of the second controllable valve 24 for regulating the pressure at the input end of the second controllable valve 24 and therefore limiting a maximum pressure at the output end of the second controllable valve 24 when it assumes its fully open configuration.

Embodiment 8. The aerosol generating nozzle system according to one of embodiments 1-7, further comprising:

- an aerosol chamber 10 connected with the aerosol exit orifice 15 to receive aerosol exiting through the aerosol exit orifice 15 into the aerosol chamber 10; and
- a counterflow gas tube 8 having a counterflow gas tube exit opening 16 opposite of the aerosol exit orifice 15 and spaced therefrom for arresting the aerosol exiting through the aerosol exit orifice 15 into the aerosol chamber 10.

Embodiment 9. The aerosol generating nozzle system according to embodiment 8, wherein the counterflow gas tube 8 is connected via a counterflow gas tube supply line 14 with a gas source 20 and a third controllable valve 28 is provided in the counterflow gas tube supply line 14 for modulating a third gas pressure in the counterflow gas tube 8, wherein the controller 3 controls the third controllable valve 28.

Embodiment 10. The aerosol generating nozzle system according to embodiment 8 or 9, wherein the third controllable valve 28 has an input end and an output end and a third adjustable pressure regulator 27 is provided upstream of the input end of the third controllable valve 28 for regulating the pressure at the input end of third controllable valve 28 and therefore limiting a maximum pressure at the output end of the third controllable valve 28 when it assumes its fully open configuration.

Embodiment 11. The aerosol generating nozzle system according to one of embodiments 8-10, wherein the aerosol chamber 10 has an aerosol chamber input end 79 accommodating the aerosol exit orifice 15 and the counterflow tube 8 and an aerosol chamber output end 80 downstream of the aerosol exit orifice 15 and the counterflow tube 8, said aerosol chamber output end 80 being connected to a concentrator 105 dividing an aerosol volume flow through the aerosol chamber 10 in a respirable volume flow including a least 70% of aerosol particles at a concentrator respirable aerosol output end 118 and an exhaust volume flow including 30% or less of the aerosol particles at a concentrator exhaust gas output end 111.

Embodiment 12. The aerosol generating nozzle system according to embodiment 11, further comprising a bidirectional valve assembly 130 having a bidirectional valve assembly input 131 that connects with the concentrator respirable aerosol output end 118, alternatingly opening the aerosol delivery channel port 136 while closing an aspiration port 137 for enabling inhaling of the aerosol by a patient, and conversely closing the aerosol delivery channel port 136 while opening an aspiration port 137 for enabling exhaling by a patient.

Embodiment 13. The aerosol generating nozzle system according to embodiment 12, wherein the controller 3 is configured to control the first valve 26 and second valve 24 so that aerosol generation takes place while the aerosol delivery channel port 136 is controlled to be open for inhalation by the bidirectional valve assembly 130, and conversely stop aerosol generation by controlling the first valve 26 and the second valve 24 while the bidirectional valve assembly 130 has closed the aerosol delivery channel port 136 while opening an aspiration port 137 for enabling exhaling by a patient.

Embodiment 14. The aerosol generating nozzle system according to one of embodiments 8-10, wherein the aerosol chamber 10 has an aerosol chamber input end 79 accommodating the aerosol exit orifice 15 and the counterflow tube 8 and an aerosol chamber output end 80 downstream of the aerosol exit orifice 15 and the counterflow tube 8, said aerosol chamber output end 80 being connected to an output cone 89.

Embodiment 15. The aerosol generating nozzle system according to embodiment 14, further comprising a bidirectional valve assembly 130 having a bidirectional valve assembly input 131 that connects with the output cone 89, alternatingly opening the aerosol delivery channel port 136 while closing an aspiration port 137 for enabling inhaling of the aerosol by a patient, and conversely closing the aerosol delivery channel port 136 while opening an aspiration port 137 for enabling exhaling by a patient.

Embodiment 16. The aerosol generating nozzle system according to one of embodiments 1-15, further comprising a pressure relief valve connected to a plenum 124 through which the respirable aerosol volume flow passes prior to inhaling by a patient for keeping the pressure of the respirable aerosol to be inhaled by a patient at a predefined pressure.

Embodiment 17. A method of generating by an aerosol generating nozzle system a respirable aerosol from a liquid solution or liquid suspension, the method comprising:

supplying liquid solution or liquid suspension at a liquid pressure, and supplying a pressurized aerosolizing gas at a pressurized aerosolizing gas pressure to an aerosol generating nozzle 7 having an aerosol exit orifice 15;

releasing the liquid solution or liquid suspension and pressurized aerosolizing gas into an aerosolizing space 73 encompassing a fluid exit 75 ejecting the liquid solution or liquid suspension into the aerosolizing space 73 where an aerosol is generated; and controlling a liquid pressure and an aerosolizing gas pressure by a controller 3 modulating at least the pressurized aerosolizing gas pressure so that alternatingly a gas pressure of the pressurized aerosolizing gas in the aerosolizing space 73 exceeds and drops below a fluid pressure at the fluid exit 75, controlling an aerosol generation duration by the time the pressurized aerosolizing gas pressure is kept by the controller 3 below the fluid pressure at the fluid exit 75.

Embodiment 18. The method according to embodiment 17, further comprising shutting off the supply of liquid solution or liquid suspension by shutting off a liquid supply line 11.

Embodiment 19. The method according to embodiment 17 or 18, further comprising modulating a third gas pressure in a counterflow gas tube 8 opposing the aerosol exit orifice 15 for arresting the aerosol exiting the aerosol exit orifice 15 into an aerosol chamber 10 connected with the aerosol exit orifice 15.

Embodiment 20. The method according to one of embodiments 17-19, further comprising a pressure relief valve connected to a plenum 124 through which a respirable aerosol volume flow passes for keeping the pressure of the respirable aerosol to be inhaled by a patient at a predefined pressure.

Embodiment 21. The method according to one of embodiments 17-20, further comprising alternatingly opening an aerosol delivery channel port while closing an aspiration port 137 for enabling inhaling of the respirable aerosol by a patient, and conversely closing the aerosol delivery channel port 136 while opening the aspiration port 137 for enabling exhaling by a patient.

Embodiment 22. The method according to embodiment 21, further comprising controlling the first valve 26 and second valve 24 so that aerosol generation takes place while the aerosol delivery channel port 136 is controlled to be open for inhalation, and conversely stop aerosol generation by controlling the first valve 26 and the second valve 24 while the aerosol delivery channel port 136 while opening an aspiration port 137 for enabling exhaling by a patient.

Embodiment 23. The method according to one of embodiments 17-22, further comprising concentrating the aerosol by a concentrator 105 dividing the aerosol volume flow into a respirable volume flow including a least 70% of aerosol particles at a concentrator respirable aerosol output end 118 and an exhaust volume flow including 30% or less of the aerosol particles at a concentrator exhaust gas output end 111.

Embodiment 24. The method according to one of embodiments 17-23, wherein the liquid solution or liquid suspension contains a surfactant.

Embodiment 25. The method according to one of embodiments 17-24, wherein the respirable aerosol has a fine particles size distribution of 1.5-6 μm MMAD.

Embodiment 26. The method according to one of embodiments 17-25, wherein the liquid solution or liquid suspension has a viscosity of 6 to 50 cSt.

The following is a list of reference numerals as shown in the drawings:

console 1
patient/clinician interface 2
microcontroller 3
hardware controller 4
internal hardware 5
liquid dispenser 6
aerosol nozzle 7
counter flow tube 8
aerosol delivery respiratory support 9
aerosol chamber 10
liquid supply line 11
gas supply line 12
gas supply line 13 counterflow gas tube supply line 14
aerosol exit orifice 15
counterflow gas tube exit opening 16
high pressure source 20
system pressure regulator 21
liquid pressure regulator 22
liquid vial 23
3-2 way solenoid valve V1 24
nozzle gas regulator 25
three-way solenoid valve V2 26
regulator R3 27
3-2-way solenoid valve V3 28
5-2-way solenoid valve V4 29
two pneumatic lines 31
dispenser cap 41
dispenser mount 42
pneumatic actuator 43
cut threads 44
half turn threads 45
threaded holes 46
threaded port 47
hollow channel 48
cantilever clips 50
slots 51
keys 52
sliding tracks 53
through channel 56
O-rings 57
liquid delivery port 58
nozzle liquid input 60
knob 65
barrel 66
liquid jet nozzle tip 67
nozzle cap 68
threads 69
liquid microchannel 70
air microchannels 71
hole 72
aerosolization space 73
gas exit 74
fluid exit 75
aerosol chamber input end 79
aerosol chamber output end 80
first O-ring annulus 81
air annulus 82
second O-ring annulus 83
common port 84
access port 85
ribs 86
pedestal 87
matching slots 88
cone 89
lip seal 90
small drain hole 91
inbuilt reservoir 92
cone input end 93
cone output end 94
cross concentrator 105
input housing part 106
output housing part 107
patterned mold 108
input tube 109
output tube 110
exhaust port 111
lobes 112
lobe molds 113
lip seal 114
concentrator input mating surface 115
concentrator output mating surface 116
concentrator input end 117
concentrator output end 118
input tube entrance port 119
input tube exit port 120
output tube entrance port 121
output tube exit port 122
gap 123
plenum 124
Bidirectional valve assembly 130
bidirectional valve assembly input 131
cylindrical disc 132
pivot pin 133
set screw 134
first seat 135
aerosol delivery channel port 136
aspiration port 137
second seat 138
bidirectional valve assembly output 139

What is claimed is:

1. An aerosol generating nozzle system for generating a respirable aerosol from a liquid solution or liquid suspension, comprising:

an aerosol generating nozzle having an aerosol exit orifice;

a fluid source for supplying the liquid solution or liquid suspension to be aerosolized through a liquid supply line to an input of the aerosol generating nozzle at a liquid pressure;

a first gas supply line connected to gas input of the nozzle for supplying pressurized aerosolizing gas at a pressurized aerosolizing gas pressure to the nozzle;

a first controllable valve for modulating the pressurized aerosolizing gas pressure; and a controller connected to the first controllable valve for controlling the same to modulate the pressurized aerosolizing gas pressure; wherein the nozzle comprises a fluid exit, a pressurized aerosolizing gas exit, and an internal aerosolizing space connected to the fluid exit at the fluid exit where the liquid solution or liquid suspension enters the aerosolizing space and the internal aerosolizing space is connected to the pressurized aerosolizing gas exit at the pressurized aerosolizing gas exit where the pressurized aerosolizing gas enters the aerosolizing space encompassing the fluid exit; wherein the controller is configured to modulate the pressurized aerosolizing gas pressure so that a gas pressure of the pressurized aerosolizing gas in the aerosolizing space exceeds and drops below a fluid pressure at the fluid exit in an alternating fashion, wherein an aerosol generation duration is controlled by a time the pressurized aerosolizing gas pressure is kept by the controller below a fluid pressure at the fluid exit.

2. The aerosol generating nozzle system according to claim 1, wherein the first controllable valve has an input end and an output end and a first adjustable pressure regulator is provided upstream of the input end of first controllable valve for regulating the pressure at the input end of first controllable valve and therefore limiting a maximum pressure at the output end of the first controllable valve when the first controllable valve assumes a fully open configuration.

3. The aerosol generating nozzle system according to claim 1, further comprising a second controllable valve for adjusting the liquid pressure in the liquid supply line.

4. The aerosol generating nozzle system according to claim 3, wherein the fluid source is a container having an input connected to a second gas supply line and an output connected to the liquid supply line and the second controllable valve is provided in the second gas supply line for modulating a second gas pressure that equals the liquid pressure in the container, wherein the controller controls the second controllable valve.

5. The aerosol generating nozzle system according to claim 4, wherein the controller is configured to hold the second gas pressure that equals the liquid pressure in the container essentially constant while performing several duty cycles of modulating the pressurized aerosolizing gas pressure so that the gas pressure of the pressurized aerosolizing gas in the aerosolizing space exceeds and drops below in an alternating fashion while maintaining the essentially constant fluid pressure at the fluid exit.

6. The aerosol generating nozzle system according to claim 3, wherein the second controllable valve has an input end and an output end and an adjustable pressure regulator is provided upstream of the input end of the second controllable valve for regulating the pressure at the input end of the second controllable valve and therefore limiting a maximum pressure at the output end of the second controllable valve when the second controllable valve assumes a fully open configuration.

7. The aerosol generating nozzle system according to claim 1, wherein a check valve is provided in the liquid supply line, preventing a volume flow back from the nozzle towards the fluid source.

8. The aerosol generating nozzle system according to claim 1, further comprising: an aerosol chamber connected with the aerosol exit orifice to receive aerosol exiting through the aerosol exit orifice into the aerosol chamber; and a counterflow gas tube having a counterflow gas tube exit opening opposite of the aerosol exit orifice and spaced therefrom for arresting the aerosol exiting through the aerosol exit orifice into the aerosol chamber.

9. The aerosol generating nozzle system according to claim 8, wherein the counterflow gas tube is connected via a counterflow gas tube supply line with a gas source and a third controllable valve is provided in the counterflow gas tube supply line for modulating a third gas pressure in the counterflow gas tube, wherein the controller controls the third controllable valve.

10. The aerosol generating nozzle system according to claim 9, wherein the third controllable valve has an input end and an output end and a third adjustable pressure regulator is provided upstream of the input end of the third controllable valve for regulating the pressure at the input end of third controllable valve and therefore limiting a maximum pressure at the output end of the third controllable valve when the third controllable valve assumes a fully open configuration.

11. The aerosol generating nozzle system according to claim 8, wherein the aerosol chamber has an aerosol chamber input end accommodating the aerosol exit orifice and the counterflow tube and an aerosol chamber output end downstream of the aerosol exit orifice and the counterflow tube, said aerosol chamber output end being connected to a concentrator dividing an aerosol volume flow through the aerosol chamber in a respirable volume flow including a least 70% of aerosol particles at a concentrator respirable aerosol output end and an exhaust volume flow including 30% or less of the aerosol particles at a concentrator exhaust gas output end.

12. The aerosol generating nozzle system according to claim 11, further comprising a bidirectional valve assembly having a bidirectional valve assembly input that connects with the concentrator respirable aerosol output end, alternatingly opening the aerosol delivery channel port while closing an aspiration port for enabling inhaling of the aerosol by a patient, and conversely closing the aerosol delivery channel port while opening the aspiration port for enabling exhaling by the patient.

13. The aerosol generating nozzle system according to claim 12, further comprising a second controllable valve for adjusting the liquid pressure in the liquid supply line, wherein the controller is configured to control the first controllable valve and the second controllable valve so that aerosol generation takes place while the aerosol delivery channel port is controlled to be open for inhalation by the bidirectional valve assembly, and conversely stop aerosol generation by controlling the first controllable valve and the second controllable valve while the bidirectional valve assembly has closed the aerosol delivery channel port while opening the aspiration port for enabling exhaling by the patient.

14. The aerosol generating nozzle system according to claim 8, wherein the aerosol chamber has an aerosol chamber input end accommodating the aerosol exit orifice and the counterflow tube and an aerosol chamber output end downstream of the aerosol exit orifice and the counterflow tube, said aerosol chamber output end being connected to an output cone.

15. The aerosol generating nozzle system according to claim 14, further comprising a bidirectional valve assembly having a bidirectional valve assembly input that connects with the output cone, alternatingly opening the aerosol delivery channel port while closing an aspiration port for enabling inhaling of the aerosol by a patient, and conversely closing the aerosol delivery channel port while opening the aspiration port for enabling exhaling by the patient.

16. The aerosol generating nozzle system according to claim 1, further comprising a pressure relief valve connected to a plenum, whereby the respirable aerosol volume flow passes the plenum prior to being inhaled by a patient for keeping the pressure of the respirable aerosol to be inhaled by the patient at a predefined pressure.

17. A method of generating by the aerosol generating nozzle system of claim 1 the respirable aerosol from the liquid solution or liquid suspension, the method comprising:

supplying the liquid solution or liquid suspension at the liquid pressure, and supplying the pressurized aerosolizing gas at the pressurized aerosolizing gas pressure to the aerosol generating nozzle having the aerosol exit orifice;

releasing the liquid solution or liquid suspension and pressurized aerosolizing gas into the aerosolizing space encompassing the fluid exit ejecting the liquid solution or liquid suspension into the aerosolizing space where the aerosol is generated; and controlling the liquid pressure and the aerosolizing gas pressure by the controller modulating at least the pressurized aerosolizing gas pressure so that alternatingly the gas pressure of the pressurized aerosolizing gas in the aerosolizing space exceeds and drops below a fluid pressure at the fluid exit, controlling an aerosol generation duration by the time the pressurized aerosolizing gas pressure is kept by the controller below the fluid pressure at the fluid exit.

18. The method according to claim 17, further comprising shutting off the supply of liquid solution or liquid suspension by shutting off the liquid supply line.

19. The method according to claim 17, further comprising modulating a counterflow gas pressure in a counterflow gas tube opposing the aerosol exit orifice for arresting the aerosol exiting the aerosol exit orifice into an aerosol chamber connected with the aerosol exit orifice.

20. The method according to claim 17, further comprising a pressure relief valve connected to a plenum through which a respirable aerosol volume flow passes for keeping the pressure of the respirable aerosol to be inhaled by a patient at a predefined pressure.

21. The method according to claim 17, further comprising alternatingly opening an aerosol delivery channel port while closing an aspiration port for enabling inhaling of the respirable aerosol by a patient, and conversely closing the aerosol delivery channel port while opening the aspiration port for enabling exhaling by a patient.

22. The method according to claim 21, the aerosol generating nozzle system further comprising a second controllable valve for adjusting the liquid pressure in the liquid supply line, the method, further comprising controlling the first controllable valve and the second controllable valve so that aerosol generation takes place while the aerosol delivery channel port is controlled to be open for inhalation, and conversely stop aerosol generation by controlling the first valve and the second valve while the aerosol delivery channel port while opening the aspiration port for enabling exhaling by a patient.

23. The method according to claim 17, further comprising concentrating the aerosol by a concentrator dividing the aerosol volume flow into a respirable volume flow including a least 70% of aerosol particles at a concentrator respirable aerosol output end and an exhaust volume flow including 30% or less of the aerosol particles at a concentrator exhaust gas output end.

24. The method according to claim 17, wherein the liquid solution or liquid suspension contains a surfactant.

25. The method according to claim 17, wherein the respirable aerosol has a fine particles size distribution of 1.5-6 μm MMAD.

26. The method according to claim 17, wherein the liquid solution or liquid suspension has a viscosity of 6 to 50 cSt.

* * * * *